United States Patent [19]
Jones et al.

[11] Patent Number: 5,866,391
[45] Date of Patent: Feb. 2, 1999

[54] ASPERGILLUS PORPHOBILINOGEN SYNTHASES AND NUCLEIC ACIDS ENCODING SAME

[75] Inventors: Aubrey Jones, Woodland; Joel R. Cherry, Davis, both of Calif.

[73] Assignee: Novo Nordisk Biotech, Inc., Davis, Calif.

[21] Appl. No.: 871,268

[22] Filed: Jun. 9, 1997

Related U.S. Application Data

[60] Provisional application No. 60/019,529 Jun. 10, 1996.
[51] Int. Cl. [6] ............................... C12N 9/00; C12Q 1/68
[52] U.S. Cl. ................................. 435/183; 435/6
[58] Field of Search .......................... 435/183, 6

[56] References Cited

FOREIGN PATENT DOCUMENTS

WO 93/03185   2/1993   WIPO .

OTHER PUBLICATIONS

Myers, et al., Journal of Biological Chemistry, vol. 262, No. 35, pp. 16822–16829 (Dec. 15, 1987).
Mitchell, et al., Journal of Biological Chemistry, vol. 270, No. 41, pp.24054–24059 (Oct. 13, 1995).
E.K. Jaffe, Journal of Bioenergetics and Biomembranes, vol. 27, No. 2 (Apr. 1995).
Myers et al., J. Biol. Chem., vol. 262, No. 35, pp. 16822–16829, 1987.

*Primary Examiner*—Rebecca E. Prouty
*Assistant Examiner*—Peter P. Tung
*Attorney, Agent, or Firm*—Steven Z. Zelson, Esq.; Elias J. Lambiris, Esq.; Robert L. Starnes

[57] ABSTRACT

The present invention relates to Aspergillus porphobilinogen synthases and isolated nucleic acid fragments comprising nucleic acid sequences encoding the porphobilinogen synthases as well as nucleic acid constructs, vectors, and recombinant host cells comprising the nucleic acid sequences. The invention also relates to methods of producing the porphobilinogen synthases.

9 Claims, 9 Drawing Sheets

```
CTGGACCAATGGTAACCCTCCGTAATTGCCTTACAGATTTAGCCCAGGGGGGTTATGGTATCCTTGGGTA         70
TTGAGGCCTGGAAATTTTTTTAGCCACCAGTTTACAGCCAGTTTCCGTTTGTAAATATTTCACATCCCCC        140
GACCCTGTCCCAATACAATAATTTTTTCGCTATATATAACGCCCCTAGCGTTGTTTTATGATCCTTAAAT        210
CCTTACTTGTACCTGAAAATTGCAACAAATGTACTGACCTGGATCGCTGGCCATTTATATCATTGCCCTG        280
CGAAGTCGTATTCTGCCAGTGGCACAGGCGCTATTCTCTTTTCTTCCCTCCACCGCGTTTCTATCTTCCA        350
TAGCACCCCACTTGCTTGCCGCTCCTGTCATTATGTCCTTTTCTAATCTCGTCTCTGACCTCGCCTTCAG        420
                         M  S  F  S  N  L  V  S  D  L  A  F  R
AGATTCTCATGATGACCGAAGTTCTCAGATATCTCAGGTACAATCGCAAGCCACTGCACGATCGTATACA        490
 D  S  H  D  D  R  S  S  Q  I  S  Q  V  Q  S  Q  A  T  A  R  S  Y  T
AGCACAGCTGCCACAAGCGTCAGCATATCTGGCGACATCTCAAGCCAGCTTCATTCCGGTTACAGCCATC        560
  S  T  A  A  T  S  V  S  I  S  G  D  I  S  S  Q  L  H  S  G  Y  S  H
CACTGAGCCGATCATGGCAGGCTGAAAGACAGTTGACTAAAGTCCGCATTTTCTTTTGTATTTACTGAGC        630
 P  L  S  R  S  W  Q  A  E  R  Q  L  T  K
TGCTCTAACCCCGAGATAGGAAATGCTTATTTATCCTCTCTTCATCACCGATAATCCCGATGAGGAGACT        700
 . . . . . . . . . . . .  E  M  L  I  Y  P  L  F  I  T  D  N  P  D  E  E  T
CCTATCCCGTCTCTCCCTGGACAGTATCGTCGAGGATTAAACCGTCTAGTTCCTTTCATCAAACCACTTG        770
  P  I  P  S  L  P  G  Q  Y  R  R  G  L  N  R  L  V  P  F  I  K  P  L
CCCACAAGGGGCTACGCTCAGTCATCCTGTTTGGCGTCCCACTACACCCCTCTGCGAAGGATGCACTAGG        840
 A  H  K  G  L  R  S  V  I  L  F  G  V  P  L  H  P  S  A  K  D  A  L  G
TACCGCTGCAGACGATCCATCTGGACCGGTAATTCAAGCTATTCGCTTGCTTAGGTCGCGGTTTCCTCAA        910
  T  A  A  D  D  P  S  G  P  V  I  Q  A  I  R  L  L  R  S  R  F  P  Q
CTTTATATCGTGACAGATGTGTGCCTTTGCGAGTATACTTCGCATGGCCACTGTGGGATACTGCGAGAAG        980
 L  Y  I  V  T  D  V  C  L  C  E  Y  T  S  H  G  H  C  G  I  L  R  E
ATGGGACTCTTGATAATACACAGTCTGTGGATCGGATTTCGGATGTTGCTCTGGCTTATGCTGCCGCCGG       1050
 D  G  T  L  D  N  T  Q  S  V  D  R  I  S  D  V  A  L  A  Y  A  A  A  G
AGCCCATTGTGTCGCTCCGTCTGATATGAATGATGGGCGAGTGCGTGCTATAAAACTGAAGCTTATTGAA       1120
  A  H  C  V  A  P  S  D  M  N  D  G  R  V  R  A  I  K  L  K  L  I  E
GCCGGGATGGCCCACCGTGTCCTACTGATGTCCTACAGCGCCAAATTTAGCGGTTGTTTGTACGGCCCTT       1190
 A  G  M  A  H  R  V  L  L  M  S  Y  S  A  K  F  S  G  C  L  Y  G  P
TCCGTGATGCAGCGGGGTCCTGCCCATCATTCGGGGATCGCAGATGCTACCAGTTACCACCCGGAGGCCG       1260
 F  R  D  A  A  G  S  C  P  S  F  G  D  R  R  C  Y  Q  L  P  P  G  G  R
TGGACTTGCTCGGCGCGCTATACAGAGAGATATAGGCGAAGGGGCAGACATCATAATGGTAAAGCCGGCG       1330
  G  L  A  R  R  A  I  Q  R  D  I  G  E  G  A  D  I  I  M  V  K  P  A
AGCAGCTACCTGGACATTATCAGAGACGCAAAAGAAATTGCCAAAGACATTCCCATTGCTGCTTACCAGG       1400
 S  S  Y  L  D  I  I  R  D  A  K  E  I  A  K  D  I  P  I  A  A  Y  Q
TCAGCGGTGAGTATGCTATGATACATGCTGGTGCCAAGGCGGGCGTATTTGACTTGAAATCCATGGCCTT       1470
 V  S  G  E  Y  A  M  I  H  A  G  A  K  A  G  V  F  D  L  K  S  M  A  F
TGAAAGTACTGAAGGGATTATAAGGGCTGGTGCTGGGATTATAGTAAGCTATTTCGTGCCTGATTTTCTA       1540
  E  S  T  E  G  I  I  R  A  G  A  G  I  I  V  S  Y  F  V  P  D  F  L
GATTGGCTTTCGAAATGATTTAGCTAGATGGAGCGTGATGAAAGCATCCACCAGATAAATAGCAGTGACG       1610
 D  W  L  S  K
ATCGCGTTTGAATCATACCTATTGGAGTAGAAGTCTCGGTATCTCGTTGGGGATTCTCTAGGTTGCTTAT       1680
TTAACGTAATGCCACGCCATGTGTTATATATTGCCTAAATACTTTTATAAAAGATACACCAAGCTGATGG       1750
TGCCAAGTGACCACTTCTAATAAATACAATTATACCAATTCCTCCGAAATATGCGGG        1807
```

FIG. 2

```
  1  M S Q S F - - - - - - - - - - - - - - - - - - - - - - - - -   B. subtilis hemB
  1  - T D L I - - - - - - - - - - - - - - - - - - - - - - - - -   E. coli hemB
  1  M - - - - - - - - - - - - - - Q P Q - - - - - - - - - - - -   human hemB
  1  - - - - - - - - - - - - - - - H T F V D L K S P F T L S N Y   pea hemB
  1  M - - - - - - - - - - - - - - - H H Q - - - - - - - - - - -   rat hemB
  1  M M A S T F N I P C N A G T I K N F N N S Q R N L G F S S N   spinach hemB
  1  M - - - - - - - - - - - - - - - H T A E F L E - - - - - - -   yeast hemB
  1  M - - - - - - - - - - - - - - S F S N L V S D L A F R D -     Ao hemB 6  - - - - - - - - - - - - - - - - - - - - - - - - - - - - -   B. subtilis hemB
  5  - - - - - - - - - - - - - - - - - - - - - - - - - - - - -   E. coli hemB
  5  - - - - - - - - - - - - - - - - - - - - - - - - - - - - -   human hemB
 16  L S F S S S K R R - - - - - - - - Q P P S L F T V R A S D S   pea hemB
  5  - - - - - - - - - - - - - - - - - - - - - - - - - - - - -   rat hemB
 31  L G I N F A K T R F S N C G D S G R I P S Q L V V R A S E R   spinach hemB
  9  - - - - - - - - - - - - - - - - - - - - - - - - - - - - -   yeast hemB
 15  - - - - - - - - - - - - - - - - - - - - - - S H D D R         Ao hemB 6  - - - - - - - - - - - - - - - - - - - - - - - - - - - - -   B. subtilis hemB
  5  - - - - - - - - - - - - - - - - - - - - - - - - - - - - -   E. coli hemB
  5  - - - - - - - - - - - - - - - - - - - - - - - - - - - - -   human hemB
 38  - - - - - - - - - - - - - D F E A A V V A G K V P E A P P     pea hemB
  5  - - - - - - - - - - - - - - - - - - - - - - - - - - - - -   rat hemB
 61  R D N L T Q Q K T G L S I E E C E A A V V A G N A P S A P P   spinach hemB
  9  - - - - - - - - - - - - - - - - - - - - - - - - - - - - -   yeast hemB
 20  S S Q I S Q V Q S Q A T A R S Y T S T - - - - - - - - - -     Ao hemB 6  - - - - - - - - - - - - - - - - - - - - N R H R R L R T S K   B. subtilis hemB
  5  - - - - - - - - - - - - - - - - - - - - Q R P R R L R K S P   E. coli hemB
  5  - - - - - - - - - - - - - - S V L H S G Y F H P L L R A W Q   human hemB
 54  V P P T P A S P A G T P V V P S L P I Q R R P R R N R R S P   pea hemB
  5  - - - - - - - - - - - - - - S V L H S G Y F H P L L R A W Q   rat hemB
 91  V P P T P K A P S G T P S V S P L S L G R R P R R N R T S P   spinach hemB
  9  - - - - - - - T E P T E I S S V L A G G Y N H P L L R Q W Q   yeast hemB
 39  - - A A T S V S I S G D I S S Q L H S G Y S H P L S R S W Q   Ao hemB 16  A M R E M V K E T R L H P S D F I Y P I F V V E G L E G K K   B. subtilis hemB
 15  A L P R M F E E T T L S L N D L V L P I F V E E I D D Y K     E. coli hemB
 21  T - - - - - A T T T L N A S N L I Y P I F V T D V P D D I Q   human hemB
 84  A L R S A F Q E T T L S P A N F V Y P L F I H E G E E D - T   pea hemB
 21  T - - - - - T P S T V S A T N L I Y P I F V T D V P D D V Q   rat hemB
121  V F R A A F Q E T T L S P A N V V Y P L F I H E G E E D - T   spinach hemB
 32  - - - - - - S E R Q L T K N M L I F P L F I S D N P D D F T   yeast hemB
 67  - - - - - - A E R Q L T K E M L I Y P L F I T D N P D E E T   Ao hemB 46  A V P S M P D V H H V S L D L - L K D E V A E L V K L G I Q   B. subtilis hemB
 45  A V E A M P G V M R I P E K H - L A R E I E R I A N A G I R   E. coli hemB
 46  P I T S L P G V A R Y G V K R - L E E M L R P L V E E G L R   human hemB
113  P I G A M P G C Y R L G W R H G L L E E V A K A R D V G V N   pea hemB
 46  P I A S L P G V A R Y G V N Q - L E E M L R P L V E A G L R   rat hemB
150  P I G A M P G C Y R L G W R H G L V E E V A K A R D V V V N   spinach hemB
 56  E I D S L P N I N R I G V N R - L K D Y L K P L V A K G L R   yeast hemB
 91  P I P S L P G Q Y R R G L N R - L V P F I K P L A H K G L R   Ao hemB
```

FIG. 3A

```
 75  SVIVFG--IPEE-KDDCGTQAYHDHGIVQK   B. subtilis hemB
 74  SVMTFG--ISHH-TDETGERAWREDGLVAR   E. coli hemB
 75  CVLIFGVP-SRVPKDERGSAADSEESPAIE   human hemB
143  SVVLFP-KIPDALKTPTGDEAYNEDGLVPR   pea hemB
 75  CVLIFGVP-SRVPKDEQGSAADSEDSPTIE   rat hemB
180  SIVVFP-K-PDALKSPTGDEAYNENGLVPR   spinach hemB
 85  SVILFGVPLIPGTKDPVGTAADDPAGPVIQ   yeast hemB
120  SVILFGVPLHPSAKDALGTAADDPSGPVIQ   Ao hemB 102  AITEIKEHFPEMVVVADTCLCEYTDHGHCG   B. subtilis hemB
101  MSRICKQTVPEMIVMSDTCFCEYTSHGHCG   E. coli hemB
104  AIHLLRKTFPNLLVACDVCLCPYTSHGHCG   human hemB
172  SIRLLKDKYPDLIIYTDVALDPYSSDGHDG   pea hemB
104  AVRLLRKTFPTLLVACDVCLCPYTSHGHCG   rat hemB
208  TIRMLKDKFPDLIIYTDVALDPYYYDGHDG   spinach hemB
115  GIKFIREYFPELYIICDVCLCEYTSHGHCG   yeast hemB
150  AIRLLRSRFPQLYIVTDVCLCEYTSHGHCG   Ao hemB 132  LVKDGV-ILNDESLELLAQTAVSQAKAGAD   B. subtilis hemB
131  VLCEHG-VDNDATLENLGKQAVVAAAGAD    E. coli hemB
134  LLSENGAFRAEESRQRLAEVALAYAKAGCQ   human hemB
202  IVREDGVIMNDETVHQLCKQAVAQARAGAD   pea hemB
134  LLSENGAFLAEESRQRLAEVALAYAKAGCQ   rat hemB
238  IVTQHGVIMNDETVHQLCKQAVAQARAGAD   spinach hemB
145  VLYDDGTINRERSVSRLAAVAVNYAKAGAH   yeast hemB
180  ILREDGTLDNTQSVDRISDVALAYAAAGAH   Ao hemB 161  IIAPSNMMDGFVTVIREALDKEGFVN-IPI   B. subtilis hemB
160  FIAPSAAMDGQVQAIRQALDAAGFKD-TAI   E. coli hemB
164  VVAPSDMMDGRVEAIKEALMAHGLGNRVSV   human hemB
232  VVSPSDMMDGRVGAMRVALDAEGFQH-VSI   pea hemB
164  VVAPSDMMDGRVEAIKAALLKHGLGNRVSV   rat hemB
268  VVSPSDMMDGRVGAIRAALDAEGYSN-VSI   spinach hemB
175  CVAPSDMIDGRIRDIKRGLINANLAHKTFV   yeast hemB
210  CVAPSDMNDGRVRAIKLKLIEAGMAHRVLL   Ao hemB 190  MSYAVKYSSEFYGPFRDAANSTPQFGDRKT   B. subtilis hemB
189  MSYSTKFASSFYGPFREAAGSALK-GDRKS   E. coli hemB
194  MSYSAKFASCFYGPFRDAAKSSPAFGDRRC   human hemB
261  MSYTAKYASSFYGPFREALDSNPRFGDKKT   pea hemB
194  MSYSAKFASCFYGPFRDAAQSSPAFGDRRC   rat hemB
297  MSYTAKYASSFY-----------PRFGDKKT  spinach hemB
205  LSYAAKFSGNLYGPFRDAACSAPSNGDRKC   yeast hemB
240  MSYSAKFSGCLYGPFRDAAGSCPSFGDRRC   Ao hemB 220  YQMDPANRMEALREAQSDVEEGADFLIVKP   B. subtilis hemB
218  YQMNPMNRAEGIAEYLLDEAQGADCLMVKP   E. coli hemB
224  YQLPPGARGLALRAVDRDVREGADMLMVKP   human hemB
291  YQMNPANYREALTEMREDESEGADILLVKP   pea hemB
224  YQLPPGARGLALRAVARDIQEGADILMVKP   rat hemB
317  YQMNPANYREALIETQEDESEGADILLVKP   spinach hemB
235  YQLPPAGRGLARRALERDMSEGADGIIVKP   yeast hemB
270  YQLPPGGRGLARRAIQRDIGEGADIIMVKP   Ao hemB
```

FIG. 3B

```
250 S L S Y M D I M R D V K N E F - T L P L V A Y N V S G E Y S    B. subtilis hemB
248 A G A Y L D I V R E L R E R T - E L P I G A Y Q V S G E Y A    E. coli hemB
254 G M P Y L D I V R E V K D K H P D L P L A V Y H V S G E F A    human hemB
321 G L P Y L D I I R L L R D N S - P L P I A A Y Q V S G E Y S    pea hemB
254 G L P Y L D M V Q E V K D K H P E L P L A V Y Q V S G E F A    rat hemB
347 G L P Y L D I I R L L R D N S - D L P I A A Y Q V S G E Y S    spinach hemB
265 S T F Y L D I M R D A S E I C K D L P I C A Y H V S D E Y A    yeast hemB
300 A S S Y L D I I R D A K E I A K D I P I A A Y Q V S G E Y A    Ao hemB 279 M V K A A Q N G W I K E K E I V L E I L T S M K R A G A D      B. subtilis hemB
277 M I K F A A L A G A I D E E K V V L E S L G S I K R A G A D    E. coli hemB
284 M L W H G A Q A G A F D L K A A V L E A M T A F R R A G A D    human hemB
350 M I K A G G A L K M I D E E K V M M E S L L C L R R A G A D    pea hemB
284 M L W H G A K A G A F D L R T A V L E S M T A F R R A G A D    rat hemB
376 M I K A G G V L K M I D E E K V M L E S L L C L R R A G A D    spinach hemB
295 M L H A A E K G V V D L K T I A F E S H Q G F L R A G A R      yeast hemB
330 M I H A G A K A G V F D L K S M A F E S T E G I I R A G A G    Ao hemB 309 L I I T Y H A K D - A A K W L - - - A E                        B. subtilis hemB
307 L I F S Y F A L D L A E K K I - - - L R                        E. coli hemB
314 I I I T Y Y T P Q L L - Q W L - K E E                          human hemB
380 I I L T Y F A L Q - A A R T L C G E K R                        pea hemB
314 I I I T Y F A P Q L L - K W L - K E E                          rat hemB
406 I I L T Y F A L Q - A A R C L C G E K R                        spinach hemB
325 L I I T Y L A P E F L - D W L - D E E N                        yeast hemB
360 I I V S Y F V P D F L - D W L - S - - K                        Ao hemB
```

FIG. 3C

ASPERGILLUS PORPHOBILINOGEN SYNTHASES AND NUCLEIC ACIDS ENCODING SAME

BACKGROUND OF THE INVENTION

1. Cross-Reference to Related Applications

This application claims the benefit of U.S. Provisional Application No. 60/019,529 filed Jun. 10, 1996, the contents of which are fully incorporated herein by reference.

2. Field of the Invention

The present invention relates to Aspergillus porphobilinogen synthases and isolated nucleic acid fragments comprising nucleic acid sequences encoding the porphobilinogen synthases. The invention also relates to nucleic acid constructs, vectors, and host cells comprising the nucleic acid sequences as well as methods for producing the porphobilinogen synthases.

3. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The second enzyme in the pathway is porphobilinogen synthase (also called aminolevulinic acid dehydratase) which catalyzes the condensation of two molecules of 5-aminolevulinic acid to form porphobilinogen. Porphobilinogen synthase is a rate-limiting enzyme in the heme biosynthesis pathways of *Neurospora crassa* and *Saccharomyces cerevisiae*.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

The cloning and expression of a porphobilinogen synthase gene from *Saccharomyces cerevisiae* (Labbe-Bois and Labbe, 1990, In, Dailey, H. A., ed., *Biosynthesis of Heme and Chlorophylls*, McGraw-Hill, Inc., New York, page 258) has been disclosed.

It is an object of the present invention to provide new porphobilinogen synthases and genes encoding same.

SUMMARY OF THE INVENTION

The present invention relates to substantially pure porphobilinogen synthases obtained from Aspergillus and to isolated nucleic acid fragments comprising a nucleic acid sequence which encodes an Aspergillus porphobilinogen synthase. The present invention further provides nucleic acid constructs, vectors, and recombinant host cells comprising a nucleic acid fragment of the present invention as well as methods for producing the porphobilinogen synthases.

BRIEF DESCRIPTION OF THE FIGURES

FIG. 2 shows the nucleotide and deduced amino acid sequence of the *Aspergillus oryzae* porphobilinogen synthase gene (SEQ ID NOS: 1 and 2, respectively). CAAT boxes are underlined and TATA boxes are boxed. The putative intron is identified with a dotted underline and the putative zinc finger domain is identified with a dashed underline. The library probe is identified with a dark solid underline and the active lysine is circled.

FIG. 3 shows the alignment of the deduced amino acid sequences for porphobilinogen synthases from *B. subtilis, E. coli,* human, pea, rat, spinach, yeast and *Aspergillus oryzae* (SEQ ID NOS: 22, 20, 18, 21, 19, 23, 17 and 2, respectively).

DETAILED DESCRIPTION OF THE INVENTION

Figure 1:
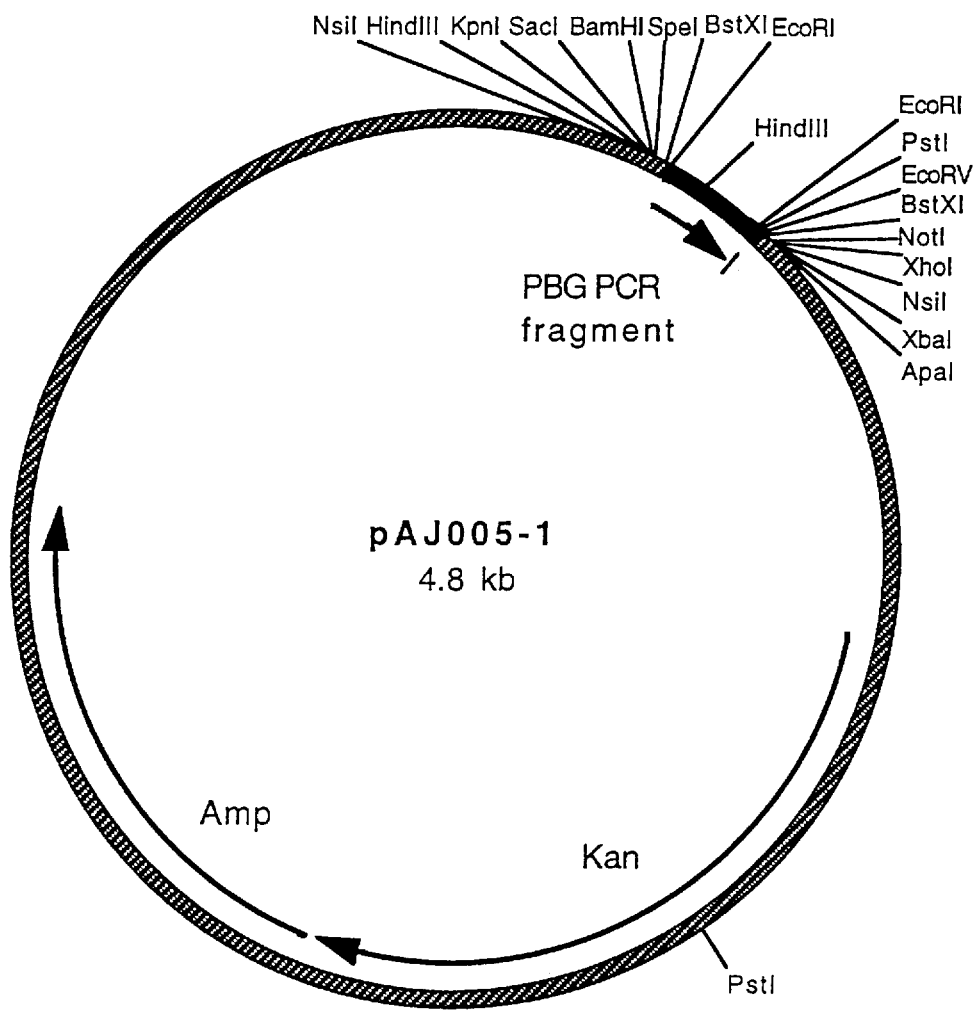
FIG. 1 shows a restriction map of plasmid pAJ005-1.

The present invention, as mentioned above, relates to porphobilinogen synthases obtained from an Aspergillus strain, e.g., porphobilinogen synthases obtained from strains of including, but not limited to, *Aspergillus foetidus, Aspergillus japonicus, Aspergillus nidulans, Aspergillus niger,* and *Aspergillus oryzae*. Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), International Mycological Institute (IMI), Agricultural Research Service Patent Culture Collection, Northern Regional Research Center (NRRL), and Institute for Fermentation in Osaka, Japan (IFO).

In a preferred embodiment, the present invention relates to porphobilinogen synthases obtained from Aspergillus. In a more preferred embodiment, the present invention relates to porphobilinogen synthases obtained from *Aspergillus oryzae*. In a most preferred embodiment, the present invention relates to porphobilinogen synthases obtained from *Aspergillus oryzae* IFO 4177 or a mutant strain thereof, e.g., the porphobilinogen synthase having the amino acid sequence set forth in SEQ ID NO:2.

The present invention also relates to porphobilinogen synthases which are encoded by nucleic acid sequences which are capable of hybridizing under high stringency conditions (i.e., prehybridization and hybridization at 45° C. in 5×SSPE, 0.3% SDS, 200 μg/ml sheared and denatured salmon sperm DNA, and 50% formamide) with a probe which hybridizes with the nucleic acid sequence set forth in SEQ ID NO:1 under the same conditions. The gene, or an oligonucleotide based thereon, can be used as a probe in Southern hybridization to isolate homologous genes of any Aspergillus species. In particular, such probes can be used for hybridization with the genomic or cDNA of the species of interest, following standard Southern blotting procedures, in order to identify and isolate the corresponding porphobilinogen synthase gene therein. Degenerate PCR primers (oligonucleotides) can be used with genomic DNA or cDNA segments to amplify porphobilinogen synthase-specific gene segments.

Identification and isolation of porphobilinogen synthase genes from a source other than those specifically exemplified herein can be achieved by utilization of the methodology described in the present examples, with publicly available Aspergillus strains.

For purposes of the present invention, the term "obtained from" means that the porphobilinogen synthase is produced by a specific source, e.g., an Aspergillus strain, or by a cell in which a gene from the source encoding the porphobilinogen synthase has been inserted.

The invention also encompasses porphobilinogen synthase variants which have at least about 50%, preferably about 55%, more preferably about 60%, even more preferably about 65%, yet even preferably about 70%, further preferably about 75%, even further preferably about 80%, and most preferably about 85%, even most preferably about 90%, and yet even most preferably about 95% homology with the amino acid sequence set forth in SEQ ID NO:2, and which qualitatively retains the activity of the porphobilinogen synthases described herein. The present invention is also directed to porphobilinogen synthase variants which have an amino acid sequence which differs by three amino acids, preferably two amino acids, and more preferably by one amino acid from the amino acid sequence set forth in SEQ ID NO:2. Each difference may be an insertion or deletion of an amino acid or the substitution of an amino acid residue by a different amino acid. Useful variants within the categories defined above include, for example, ones in which conservative amino acid substitutions have been made, which substitutions do not significantly affect the activity of the protein. By conservative substitution is meant that amino acids of the same class may be substituted by any other amino acid of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

The physical-chemical properties of the porphobilinogen synthases of the present invention may be determined using various techniques well known in the art including, but not limited to, SDS-PAGE, isoelectric focusing, and cross-reaction immunoidentity tests. The porphobilinogen synthases of the present invention may be assayed using methods known in the art.

The porphobilinogen synthases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, for example, *Protein Purification,* eds. J. -C. Janson and Lars Ryden, VCH Publishers, New York, 1989). As defined herein, a "substantially pure" porphobilinogen synthase is a porphobilinogen synthase which is essentially free of other non-porphobilinogen synthase proteins, for example, at least about 20% pure, preferably about 40% pure, more preferably about 60% pure, even more preferably about 80% pure, most preferably about 90% pure, and even most preferably at least about 95% pure, as determined by SDS-PAGE.

The present invention also relates to nucleic acid fragments comprising a nucleic acid sequence which encodes a porphobilinogen synthase of the present invention and to nucleic acid constructs comprising a nucleic acid fragment of the present invention.

In a preferred embodiment, the nucleic acid sequence encodes a porphobilinogen synthase obtained from Aspergillus. In a more preferred embodiment, the nucleic acid sequence encodes a porphobilinogen synthase obtained from *Aspergillus oryzae.* In a most preferred embodiment, the nucleic acid sequence encodes a porphobilinogen synthase obtained from *Aspergillus oryzae* IFO 4177, e.g., the nucleic acid sequence set forth in SEQ ID NO:1. The present invention also encompasses nucleic acid sequences which encode a porphobilinogen synthase having the amino acid sequence set forth in SEQ ID NO:2, which differ from SEQ ID NO:1 by virtue of the degeneracy of the genetic code. The nucleic acid sequences of the present invention encompass both the genomic sequence depicted therein as well as the corresponding cDNA and RNA sequences, and the phrase "nucleic acid sequence" as used herein will be understood to encompass all such variations including synthetic DNA.

The present invention also relates to nucleic acid constructs comprising a nucleic acid fragment of the invention. "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a preferred embodiment, the nucleic acid constructs are operably linked to regulatory regions capable of directing the expression of the porphobilinogen synthase in a suitable expression host.

The present invention also provides recombinant vectors comprising a nucleic acid construct of the present invention. In a preferred embodiment, the nucleic acid sequence is operably linked to a promoter sequence. In another preferred embodiment, the vectors of the present invention further comprise a transcription termination signal and/or a selectable marker.

The recombinant vectors of the invention are useful for the expression of an Aspergillus porphobilinogen synthase gene in active form. A useful vector contains an element that permits stable integration of the vector into the host cell genome or autonomous replication of the vector in a host cell independent of the genome of the host cell, and preferably one or more phenotypic markers which permit easy selection of transformed host cells. The vector may also include control sequences such as a promoter, ribosome binding site, translation initiation signal, and, optionally, a selectable marker or various activator or repressor sequences. To permit the secretion of the expressed protein, nucleic acids encoding a signal sequence may be inserted prior to the coding sequence of the gene. For expression under the direction of control sequences, a porphobilinogen synthase gene to be used according to the present invention is operably linked to the control sequences in such a way that expression of the coding sequence is achieved under conditions compatible with the control sequences.

The vectors carrying a nucleic acid construct of the present invention may be any vector which can conveniently be subjected to recombinant DNA procedures. The choice of a vector will typically depend on the host cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into a host cell, is integrated into the host cell genome and replicated together with the chromosome(s) into which it has been integrated. The vector system may be a single vector or plasmid or two or more vectors or plasmids which together contain the total DNA to be integrated into the genome.

In the vectors, the DNA sequence should be operably linked to a suitable promoter sequence. The promoter may be any DNA sequence which shows transcriptional activity in the host cell of choice and may be obtained from genes encoding proteins either homologous or heterologous to the host cell. Examples of suitable promoters for directing the transcription of the nucleic acid construct of the invention, especially in a bacterial host, are the promoter of the lac operon of *E. coli,* the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes, the prokaryotic β-lactamase promoter (Villa-Kamaroff et al., 1978, *Proceedings of the National Academy of Sciences USA* 75:3727–3731) or the tac promoter (DeBoer et al., 1983, *Proceedings of the National Academy of Sciences USA* 80:21–25). Further promoters are described in "Useful proteins from recombinant bacteria" in *Scientific American,* 1980, 242:74–94; and in Sambrook et al., *Molecular Cloning, A Laboratory Manual,* 2d ed., Cold Spring Harbor, N.Y., 1989. In a yeast host, a useful promoter is the eno-1 promoter. For transcription in a fungal host, examples of useful promoters are those obtained from the genes encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Preferred promoters are the TAKA-amylase, NA2-tpi, and glaA promoters.

The vectors of the invention may also comprise a suitable transcription terminator and, in eukaryotes, polyadenylation sequences operably connected to the DNA sequence encoding a porphobilinogen synthase of the present invention. Termination and polyadenylation sequences may be obtained from the same sources as the promoter. The vectors may further comprise a DNA sequence enabling the vectors to replicate in the host cell in question. Examples of such sequences are the origins of replication of plasmids pUC19, pACYC177, pUB110, pE194, pAMB1, and pIJ702.

The vectors of the present invention preferably contain one or more selectable markers which permit easy selection of transformed cells. A selectable marker is a gene the product of which provides for biocide or viral resistance, resistance to heavy metals, prototrophy to auxotrophs and the like. The selectable marker may be selected from the group consisting of, but not limited to, amdS, pyrG, argB, niaD, sC, trpC, bar, and hygB. Preferred for use in an Aspergillus cell are the amdS and pyrG markers of *Aspergillus nidulans* or *Aspergillus oryzae* and the bar marker of *Streptomyces hygroscopicus.* Furthermore, selection may be accomplished by co-transformation, e.g., as described in WO 91/17243 where the selectable marker is contained in a separate vector.

The vectors of the invention preferably also contain a signal peptide coding region, which codes for an amino acid sequence linked to the amino terminus of the heme biosynthetic enzyme, permitting the localization of the porphobilinogen synthase to a particular cellular compartment. The signal peptide coding region may be native to the first nucleic acid sequence encoding the porphobilinogen synthase or may be obtained from foreign sources. The 5' end of the coding sequence of the first nucleic acid sequence may inherently contain a signal peptide coding region naturally linked in translation reading frame with the segment of the coding region which encodes the localized porphobilinogen synthase. Alternatively, the 5' end of the coding sequence may contain nucleic acids encoding a signal peptide coding region which is foreign to that portion of the coding sequence which encodes the localized porphobilinogen synthase. The signal peptide coding region may be obtained from a *Neurospora crassa* ATPase gene (Viebrock et al., 1982, *EMBO Journal* 1:565–571) or from a *Saccharomyces cerevisiae* cytochrome c peroxidase gene (Kaput et al., 1982, *Journal of Biological Chemistry* 257:15054–15058). However, any signal peptide coding region capable of permitting localization of the 5-aminolevulinic acid synthase in a filamentous fungal host of choice may be used in the present invention.

To avoid the necessity of disrupting the cell to obtain the expressed porphobilinogen synthase, and to minimize the amount of possible degradation of the expressed porphobilinogen synthase within the cell, it is preferred that expression of the porphobilinogen synthase gene gives rise to a product secreted outside the cell. To this end, the porphobilinogen synthases of the present invention may thus comprise a preregion permitting secretion of the expressed protein into the culture medium. If desirable, this preregion may be native to the porphobilinogen synthase of the invention or substituted with a different preregion or signal sequence, conveniently accomplished by substitution of the DNA sequences encoding the respective preregions. For example, the preregion may be obtained from a glucoamylase or an amylase gene from an Aspergillus species, an amylase gene from a Bacillus species, a lipase or proteinase gene from *Rhizomucor miehei,* the gene for the α-factor from *Saccharomyces cerevisiae* or the calf preprochymosin gene. Particularly preferred is the preregion for *Aspergillus oryzae* TAKA amylase, *Aspergillus niger* neutral amylase, the maltogenic amylase from Bacillus NCIB 11837, *Bacillus stearothermophilus* α-amylase, or *Bacillus licheniformis* subtilisin. An effective signal sequence for fungal hosts is the *Aspergillus oryzae* TAKA amylase signal, the *Rhizomucor miehei* aspartic proteinase signal, or the *Rhizomucor miehei* lipase signal.

The procedures used to ligate the nucleic acid construct of the invention, the promoter, terminator and other elements, and to insert them into suitable vectors containing the information necessary for replication, are well known to persons of ordinary skill in the art (cf., for instance, Sambrook et al., *supra*).

The present invention also relates to host cells comprising a nucleic acid construct or an expression vector of the invention which are advantageously used in the recombinant production of the porphobilinogen synthases of the invention. The cell may be transformed with the nucleic acid construct of the invention, conveniently by integrating the construct into the host chromosome. This integration is generally considered to be an advantage as the sequence is more likely to be stably maintained in the cell. Integration of the construct into the host chromosome may be performed according to conventional methods, e.g., by homologous or non-homologous recombination. Alternatively, the cell may be transformed with an expression vector as described below in connection with the different types of host cells.

The choice of host cells and vectors will to a large extent depend upon the porphobilinogen synthase and its source. The host cell may be selected from prokaryotic cells, such as bacterial cells. Examples of suitable bacteria are grampositive bacteria such as *Bacillus subtilis, Bacillus licheniformis, Bacillus lentus, Bacillus brevis, Bacillus stearothernophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram-negative bacteria such as *E. coli.* The transformation of the bacteria may, for instance, be effected by protoplast transformation or by using competent cells in a manner known per se.

The host cell is preferably a eukaryote, such as a mammalian cell, an insect cell, a plant cell or preferably a fungal cell, including yeast and filamentous fungi. For example, useful mammalian cells include CHO or COS cells. A yeast host cell may be selected from a species of Saccharomyces or Schizosaccharomyces, e.g., *Saccharomyces cerevisiae.* Useful filamentous fungi may be selected from a species of Aspergillus, e.g., *Aspergillus oryzae* or *Aspergillus niger.* Alternatively, a strain of a Fusarium species, e.g., *Fusarium oxysporum* or *Fusarium graminearum,* can be used as a host cell. Fungal cells may be transformed by a process involving protoplast formation, transformation of the protoplasts, and regeneration of the cell wall in a manner known per se. A suitable procedure for transformation of Aspergillus host cells is described in EP 238 023. A suitable method of transforming Fusarium species is described by Malardier et al., 1989, *Gene* 78:147–156 or in copending U.S. Ser. No. 08/269,449.

In a particularly preferred embodiment, the expression of the porphobilinogen synthase gene is achieved in a fungal host cell, such as Aspergillus. The porphobilinogen synthase gene is ligated into a plasmid preferably containing the *Aspergillus oryzae* TAKA amylase promoter or the *Aspergillus niger* neutral amylase NA2 promoter and amdS or pyrG as the selectable marker. Alternatively, the selectable marker may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences USA* 81:1470–1474.

The present invention also relates to methods for producing a porphobilinogen synthase of the present invention comprising (a) cultivating an Aspergillus strain in a nutrient medium to produce the porphobilinogen synthase, and (b) recovering the porphobilinogen synthase.

The present invention also relates to methods for recombinantly producing a porphobilinogen synthase of the present invention comprising (a) cultivating a host cell comprising a nucleic acid construct which comprises a nucleic acid sequence encoding the porphobilinogen synthase under conditions conducive to the production of the enzyme, and (b) recovering the porphobilinogen synthase. If the expression system secretes the porphobilinogen synthase into the fermentation medium, the enzyme can be recovered directly from the medium. If the recombinant porphobilinogen synthase is not secreted, it is recovered from cell lysates.

Any method of cultivation of a cell known in the art may be used which results in the expression or isolation of a porphobilinogen synthase of the present invention. For example, cultivation may be understood as comprising shake flask cultivation, small- or large-scale fermentation (including continuous, batch, fed-batch, or solid state fermentations) in laboratory or industrial fermentors performed in a suitable medium and under conditions allowing the porphobilinogen synthase to be expressed or isolated.

The cultivation takes place in a suitable nutrient medium comprising carbon and nitrogen sources and inorganic salts using procedures known in the art (see, e.g., Bennett, J. W. and LaSure, L. (eds.), *More Gene Manipulations in Fungi,* Academic Press, CA, 1991). Suitable media are available from commercial suppliers or may be prepared according to published compositions (e.g., in catalogues of the American Type Culture Collection).

The porphobilinogen synthases produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The present invention is also directed to methods of using the porphobilinogen synthases.

The porphobilinogen synthases of the present invention may be used to increase the yield of a hemoprotein produced by a host cell, where porphobilinogen synthase is a rate-limiting step in the production of heme in the host cell, by overexpressing the nucleic acid sequence encoding the porphobilinogen synthase in the host cell. The method comprises:

(a) introducing into the host cell, which is capable of producing the hemoprotein, one or more copies of the nucleic acid sequence encoding the porphobilinogen synthase, wherein the nucleic acid sequence is operably linked to regulatory regions capable of directing the expression of the porphobilinogen synthase;

(b) cultivating the cell in a nutrient medium suitable for production of the hemoprotein and the porphobilinogen synthase; and (c) recovering the hemoprotein from the nutrient medium of the cell.

The present invention is further described by the following examples which should not be construed as limiting the scope of the invention.

EXAMPLES

Example 1:

*Aspergillus oryzae* Strain A1560 Genomic DNA Extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3M solution) was added to a final concentration of 0.3M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 µg/ml and the mixture was incubated at 37ûC for 30 minutes. Proteinase K was then added at a concentration of 200 µg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2:

Generation of a Genomic hemB Probe by PCR

Degenerate PCR primers were designed based on the amino acid sequence flanking a 126 bp hemB fragment from *Aspergillus oryzae* (Jesper Vind, 1994, Ph.D. Dissertation, University of Copenhagen, Copenhagen, Denmark) and the homologous regions of yeast and human hemB clones (Myers et al., 1987, *Journal of Biological Chemistry* 262:16822–16829; Wetmur et al., 1986, *Proceedings of the National Academy of Sciences USA* 83:7703–7707). The oligonucleotide primers were synthesized using an Applied Biosystems Model 394 DNA/RNA Synthesizer. Sense, 5'-GT(AGCT)GC(AGCT)CC(AGCT)(AT)(CG)(AGCT)GA(CT)ATGATGGA-3' (SEQ ID NO:3) and antisense 5'-GC(AG)TC(AGCT)CG/T(AG)A A(AGCT)CC(AG)TA-3' (SEQ ID NO:4) primers were used to PCR amplify the hemB fragment using pJVi 60 (Vind, 1994, *supra*) as a template. The PCR reaction (50 µl) was composed of 10 mM Tris-HCl pH 8.3, 50 mM KCl, 1.5 mM MgCl$_2$, 0.01% w/v gelatin, 200 µM each of dATP, dCTP, dGTP, and dTTP, 500 ng of pJVi 60, and 50 pmol of each PCR primer described above. The reaction was incubated at 95° C. for 3 minutes and cooled to 80° C. Then 5 units of Taq polymerase were added. The reaction was incubated in a Perkin-Elmer 9600 Thermal Cycler programmed for 35 cycles each at 95° C. for 30 seconds, 45° C. for 1 minute, and 72° C. for 1 minute. Following the last cycle the reaction was incubated at 72° C. for 5 minutes. A predicted 126 bp hemB PCR product was cloned into a pCRII vector to produce plasmid pAJ005-1 (FIG. 1).

Example 3:

*Aspergillus oryzae* Strain A1560 DNA Libraries and Identification of Porphobilinogen Synthase (hemB) Clones

*Aspergillus oryzae* strain A1560 genomic DNA libraries were constructed using the bacteriophage cloning vector λZipLox (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contained 1×10$^6$ pfu/ml.

Bacteriophage DNA from approximately 8×10$^4$ plaques was transferred to duplicate circular Nytran Plus membranes (Schleicher & Schuell, Keene, N.H.) and probed with a $^{32}$P-labeled PCR product derived by amplifying the hemB fragment of pAJ005-1 (see Example 2) according to Mertz and Rashtchian (1994, *Analytical Biochemistry* 221:160–165). The amplification reaction (50 µl) contained the following components: 10 mM Tris-HCl pH 8.3, 50mM KCl, 1.5 mM MgCl2, 0.01% (w/v) gelatin, 0.04 mM each of dATP, dCTP, dGTP, and dTTP, 5 µl of $^{32}$P-dCTP (3000 Ci/mmole, 3.3 µM; Amersham, Arlington Heights, Ill.), and 50 pmole each of sense primer 5'-GTGGCTCCGAGTGATAT-3' (SEQ ID NO:5) and antisense primer 5'-GCATCGCGAAAAGGACCG-3' (SEQ ID NO:6). The reaction was heated to 95° C. for 3 minutes followed by the addition of 5 units of Taq polymerase. The reaction was then incubated in a Perkin-Elmer Thermal Cycler programmed for 30 cycles, each cycle at 95° C. for 1 minute, 55° C. for 1 minute, and 72° C. for 1 minute. The reaction solution was passed through a Sephadex G50 column (Pharmacia, Alameda, Calif.) to remove unincorporated nucleotides and then denatured and added to the hybridization buffer. Denatured probe (10$^6$ cpm/ml) was added to hybridization buffer and incubated overnight with prehybridized membranes. Prehybridization and hybridization was conducted at 42° C. in 5×SSC, 50 mM sodium phosphate pH 7, 5×Denhardt's solution, 0.1% (w/v) SDS, 5 mM EDTA pH 8, 10 µg/mL denatured salmon sperm DNA, and 50% formamide. Membranes were washed four times in 0.1×SSC, 0.1% SDS for 15 minutes at 42° C. Primary plaques that gave a positive signal were screened a second time and purified according to the manufacturer's instructions. Ten genomic clones that produced a positive signal were excised from the λZipLox vector as pZL derivatives according to the manufacturer's instructions (Bethesda Research Laboratories, Inc., Bethesda, Md.) and sequenced according to the method of Hattori and Sakaki (1986, *Analytical Biochemistry* 152:232–237). The pZL derivatives were designated pAJ007-1 through pAJ007-10. Clone *E. coli* DH5α pAJ007-6 contained a 3.7 kb genomic fragment based on restriction mapping and was further analyzed.

Example 4:

Characterization of the Porphobilinogen Synthase (hemB) Gene

*E. coli* DH5α pAJ007-6 described in Example 2 was subjected to DNA sequencing according to the procedure described in Example 2.

The nucleotide sequence of the cloned *Aspergillus oryzae* A1560 hemB gene revealed an open reading frame of 1308 nucleotides as shown in FIG. 2 (SEQ ID NO:1) encoding a 374 amino acid polypeptide with a predicted molecular weight of 40 kDa as shown in FIG. 2 (SEQ ID NO:2). The nucleotide sequence contains one 48 bp putative intron which is flanked by splice site consensus sequences and contains an internal consensus sequence as predicted by (Unkles, 1992, in *Applied Molecular Genetics of Filamentous Fungi,* Chapter 2, J. R. Kinghorn and G. Turner, editors, Blackie Academic and Professional Publications). The 3' splice site (TAG) is located 254 bp downstream of the Met, a 5' splice site (GTCCGC) is located 46 bp upstream of the 3' splice site, and the internal consensus sequence (TCTAAC) is located 30 bp downstream of the 5' splice site. The 5' untranslated region contains two CAAT motifs at positions −377 and −233 and may play an important role in transcriptional regulation (Gurr et al., 1987, *supra*). In addition, several putative TATA like boxes are found in the 3' untranslated region (−117, −208, −650). As expected, hemB does not appear to contain a leader sequence at the N-terminus since it is cytoplasmic in other organisms except plants (Bottemley and Muller-Eberhard, 1988, *Seminars in Hematology* 25:282–302).

Amino acid alignment of the *Aspergillus oryzae* hemB gene (SEQ ID NO:2) to other hemB genes is shown in FIG. 3. The deduced hemB amino acid sequences from yeast (SEQ ID NO:17; Myers et al., 1987, *supra*), human (SEQ ID NO:18; Wetmur et al., 15 1986, *supra*), rat (SEQ ID NO:19; Bishop et al., 1989, *Nucleic Acids Research* 14:10115) and *E. coli* (SEQ ID NO:20; Li et al., 2989, *Gene* 75:177–184) have 63%, 55%, 55% and 40% identity, respectively to the *Aspergillus oryzae* hemB amino acid sequence. The deduced hemB amino acid sequences from pea (SEQ ID NO:21; Bsese et al., 1991, *Journal of Biological Chemistry* 266:17060–17066), *Bacillus subtilis* (SEQ ID NO:22; Hansson et al., 1991, *Journal of Bacteriology* 173:2590–2599) and spinach (SEQ ID NO:23; Scharmburg and Schneider-Poetsch, 1991, EMBL *Data Library*) are less similar (40%, 39% and 33% identity, respectively). However, since both the pea and spinach hemB amino acid sequences contain an N-terminal chloroplast signal sequence, their similarity to the *Aspergillus oryzae* hemB would significantly increase if they are aligned as mature polypeptides. Based on these alignments, the active lysine site of the *Aspergillus oryzae* hemB is located at amino acid 299 (Jaffe, 1995, *Journal of Bioenergetics and Biomembranes* 27:169–179) and a conserved zinc-finger like domain as predicted by Berg (1986, *Nature* 319:264–265) is located at amino acids 166–180. The zinc-finger has been suggested to prevent oxidation of the sulfhydryl groups at the active site by binding $Zn^{+2}$ (Jaffe, 1995, *supra*). The corresponding domain in plant hemB's is proposed to bind $Mg^{2+}$ rather than $Zn^{2+}$ (Bsese et al., 1991, *supra*). Interestingly, the first residue of the hemB finger domain is a Thr (at position 166) which is conserved for this position in the plant metal-binding domain. However, the remaining positions in the hemB zinc finger domain are conserved.

Example 5:

Construction of pAJ023

Figure 4:
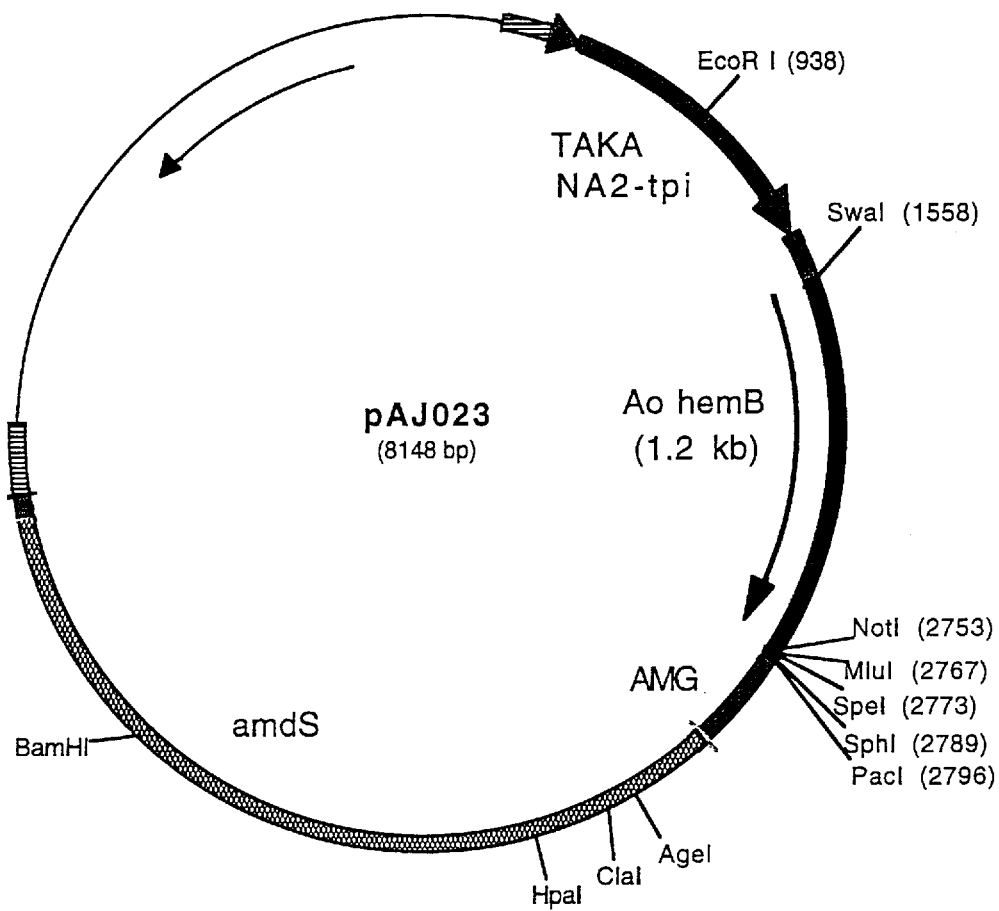
FIG. 4 shows a restriction map of pAJ023.

Plasmid pAJ023 (FIG. 4) was constructed by PCR amplifying the *Aspergillus oryzae* hemB coding region and subcloning it into the *Aspergillus oryzae* expression vector pBANE6. The amplification product was designed to contain 5' SwaI and 3' PacI restriction sites to facilitate cloning into pBANe6. The amplification reaction (50 μl) contained the following components: 10 mM Tris-HCl pH 8.3, 50 mM KCl, 1.5 mM $MgCl_2$, 0.01% (w/v) gelatin, 200 μM each of dATP, dCTP, dGTP, and dTTP, 200 ng of pAJ007-6 DNA, and 50 pmol of each PCR primer shown below:

PBG10 (Sense):
5'-GCATATTTAAATGATGTCCTTTTCTAATCTCGT-3' (SEQ ID NO:7)

PBG11A (Antisense): 5'-ATATTAATTAATCCATCTAGCTAAATCATT-3' (SEQ ID NO:8)

The underlined regions of PBG10 and PBG11A contained the cloning restriction sequences SwaI and PacI, respectively. The reaction was incubated at 95° C. for 3 minutes and cooled to 80° C. Five units of PWO (BM) polymerase were added. The reaction was incubated in a Perkin-Elmer 9600 Thermo-Cycler programmed for 30 cycles each at 95° C. for 30 seconds, 57° C. for 1 minute, and 72° C. for 1 minute. Following the last cycle, the reaction was incubated at 72° C. for 5 minutes. The final PCR product was gel purified, digested with SwaI and PacI, and ligated into the vector pBANE6 which was digested with SwaI and PacI to create pAJ023.

Example 6:

Construction of *Aspergillus oryzae* Strain JRoC50.3.18A

*Aspergillus oryzae* strain JRoC50.3.18A containing plasmid pJR0C50 was constructed as follows. *Coprinus cinereus* IFO 8371 peroxidase cDNA fragments were prepared by PCR using specific oligonucleotide primers shown below (Saiki et al., 1988, *Science* 239:487–491) constructed on the basis of the amino acid sequence of the *Coprinus macrorhizus* peroxidase (Baunsgaard et al., 1993, *European Journal of Biochemistry* 213:605–611):

1. 5'-GCGCGAATTCGTNGGNATNGGNATNAA(CT)CA(CT)GG-3' (SEQID NO:9)
2. 3'-TACAGNTT(GA)AC(GA)GGNGGCCTAGGCG-5' (SEQ ID NO:10)
3. 5'-GCGAATTCACNCCNCA(GA)GTNTT(CT)GA(CT)AC-3' (SEQ ID NO:11)
4. 3'-GGNAA(GA)GGNCCNCT(CT)AA(GA)CCTAGGCG-5' (SEQ ID NO:12)
5. 5'-GCGCGAATTCTGGCA(GA)TCNAC-3' (SEQ ID NO:13)
6. 5'-GCGCGAATTCTGGCA(GA)AGNATG-3' (SEQ ID NO:14)
7. 3'-CGNTACCGNTT(CT)TACAGCCTAGG-5' (SEQ ID NO:15)

PCR was performed using the Gene Amp Kit and apparatus (Perkin Elmer Cetus, Norwalk, Conn.) in accordance with the manufacturer's instructions with the exception that the reaction was conducted at 28° C. for the first 3 cycles in order to obtain better hybridization to the first strand cDNA (prepared from mRNA obtained from *Coprinus cinereus* strain IFO 8371) and subsequently at 65° C. for 30 cycles of PCR.

The primers were combined as follows: 1 with 2; 3 with 4; 5 with 7; 6 with 7; 1 with 4; and 3 with 7. The PCR fragments were extended with an EcoRI site at the 5'-end and a BamHI site at the 3'-end. The reactions were analyzed on a 1% agarose-TBE gel where bands of the expected size were found in all the reactions. To verify that the bands corresponded to peroxidase-specific sequences, the gel was subjected to Southern blotting and hybridized to an oligonucleotide probe with the following sequence which is positioned between primers 3 and 4:

5'-GT(CT)TC(GA)AT(GA)TAGAA(CT)TG-3' (SEQ ID NO:16)

The probe was found to hybridize to bands of approximately 130 bp, 420 bp, 540 bp, and 240 bp, thus confirming that the DNA bands observed corresponded to peroxidase sequences.

DNA from the various PCR reactions was digested with EcoRI and BamHI and cloned into the plasmid pUC19 (New England BioLabs, Beverly, Mass.). Colonies containing the correct PCR fragments were identified by hybridization using the oligonucleotide probe (SEQ ID NO:16) described above. DNA from positive colonies was analyzed by restriction mapping and partial DNA sequence analysis as described by Sanger et al. (1977, *Proceedings of the National Academy of Sciences USA* 74:5463–5467). A 430 bp fragment from one of the clones, obtained by using primers 1 and 4, was used to screen a *Coprinus cinereus* cDNA library as described below.

Figure 5:
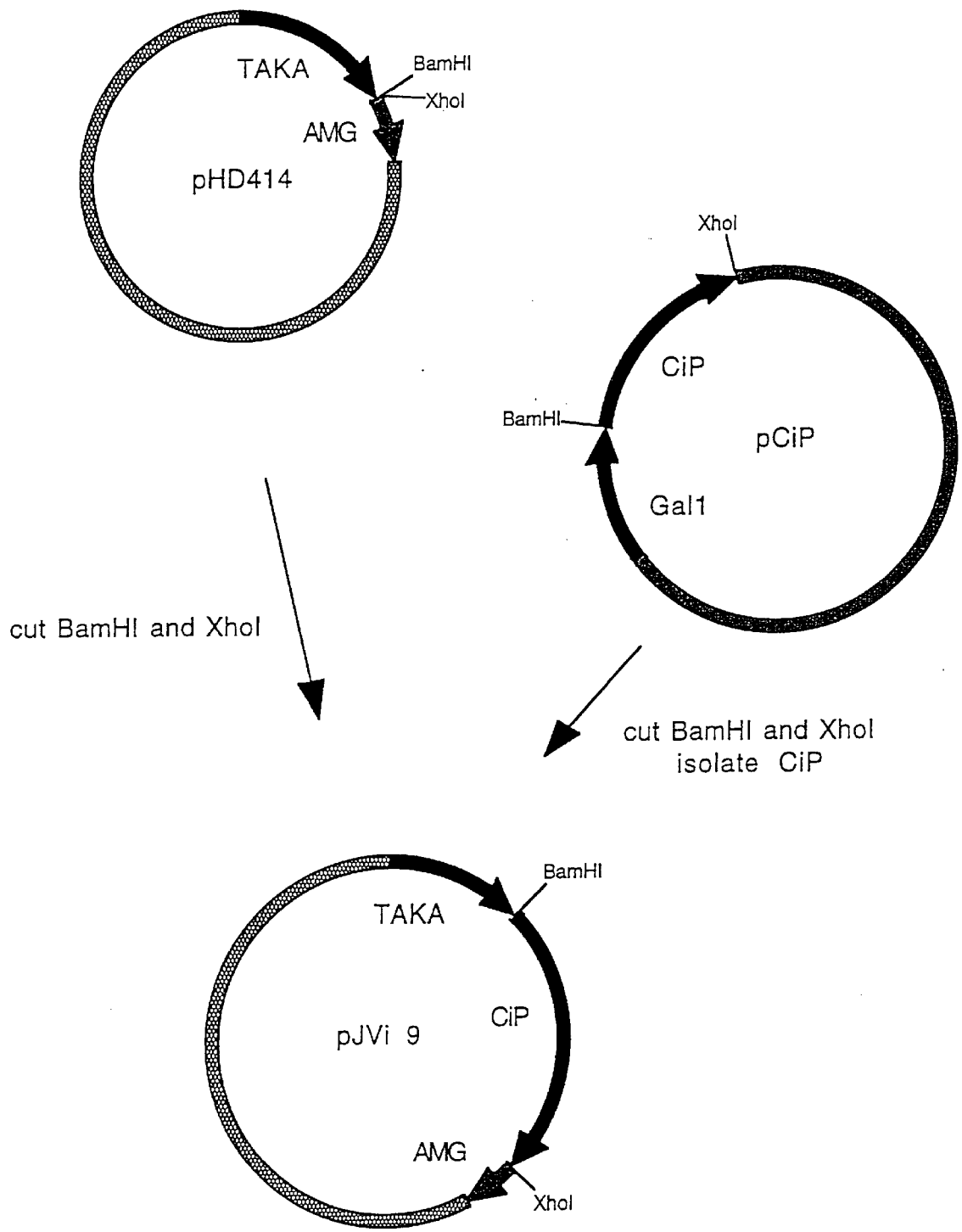
FIG. 5 shows the construction of plasmid pJVi9.

Total RNA was extracted from homogenized *Coprinus cinereus* strain IFO 8371 mycelia, collected at the time of maximum peroxidase activity according to the methods described by Boel et al. (1984, *EMBO Journal* 3:1097–1102) and Chirgwin et al. (1979, *Biochemistry* 18:5294–5299). Poly(A)-containing RNA was obtained by two cycles of affinity chromatography on oligo(dT)- cellulose as described by Aviv and Leder (1972, *Proceedings of the National Academy of Sciences USA* 69:1408–1412). cDNA was synthesized by means of a cDNA Synthesis Kit (Invitrogen, San Diego, Calif.) according to the manufacturer's instructions. Approximately 50,000 *E. coli* recombinants from the Coprinus cinereus cDNA library were transferred to Whatman 540 paper filters. The colonies were lysed and immobilized as described by Gerger et al. (1979, *Nucleic Acids Research* 7:2115–2135). The filters were hybridized with the $^{32}$P-labelled 430 bp peroxidase-specific probe in 0.2 ×SSC-0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly, 1979, *Nucleic Acids Research* 7:1513–1523), and the DNA sequences of the cDNA inserts were determined by the Sanger dideoxy procedure (Sanger et al., 1977, *Proceedings of the National Academy of Sciences USA* 74:5463–5467). One of the colonies was selected and the vector was designated pCiP. The peroxidase cDNA fragment was excised from the vector by cleavage with BamHI/XhoI and was purified by agarose gel electrophoresis, electroeluted and made ready for ligation reactions. The cDNA fragment was ligated to BamHI/XhoI digested pHD414 to generate pJVi9 wherein the cDNA was under transcriptional control of the TAKA promoter from *Aspergillus oryzae* and the AMG™ (Novo Nordisk A/S, Bagsvaerd, Denmark) terminator from *Aspergillus niger* as shown in FIG. 5.

Figure 6:
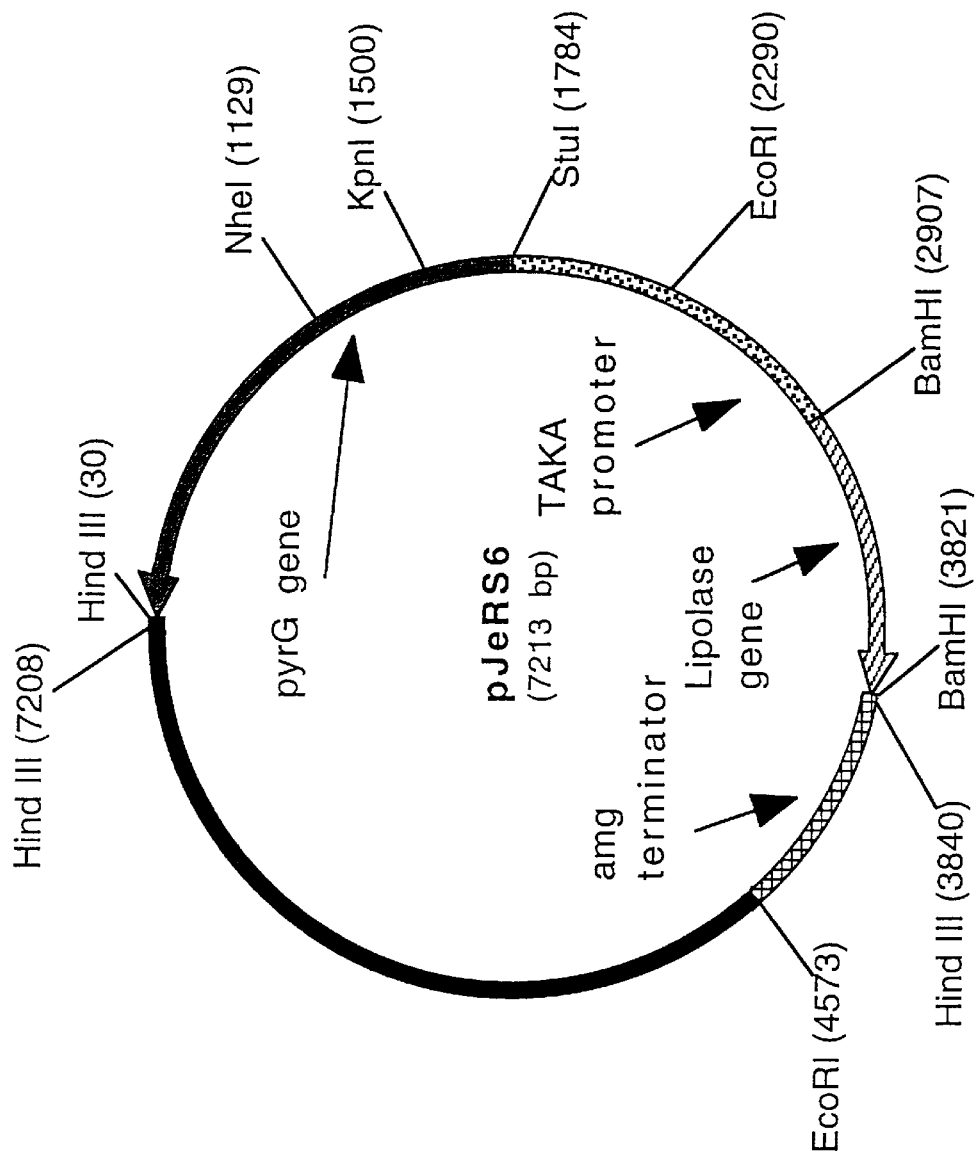
FIG. 6 shows a restriction map of plasmid pJeRS6.
Figure 7:
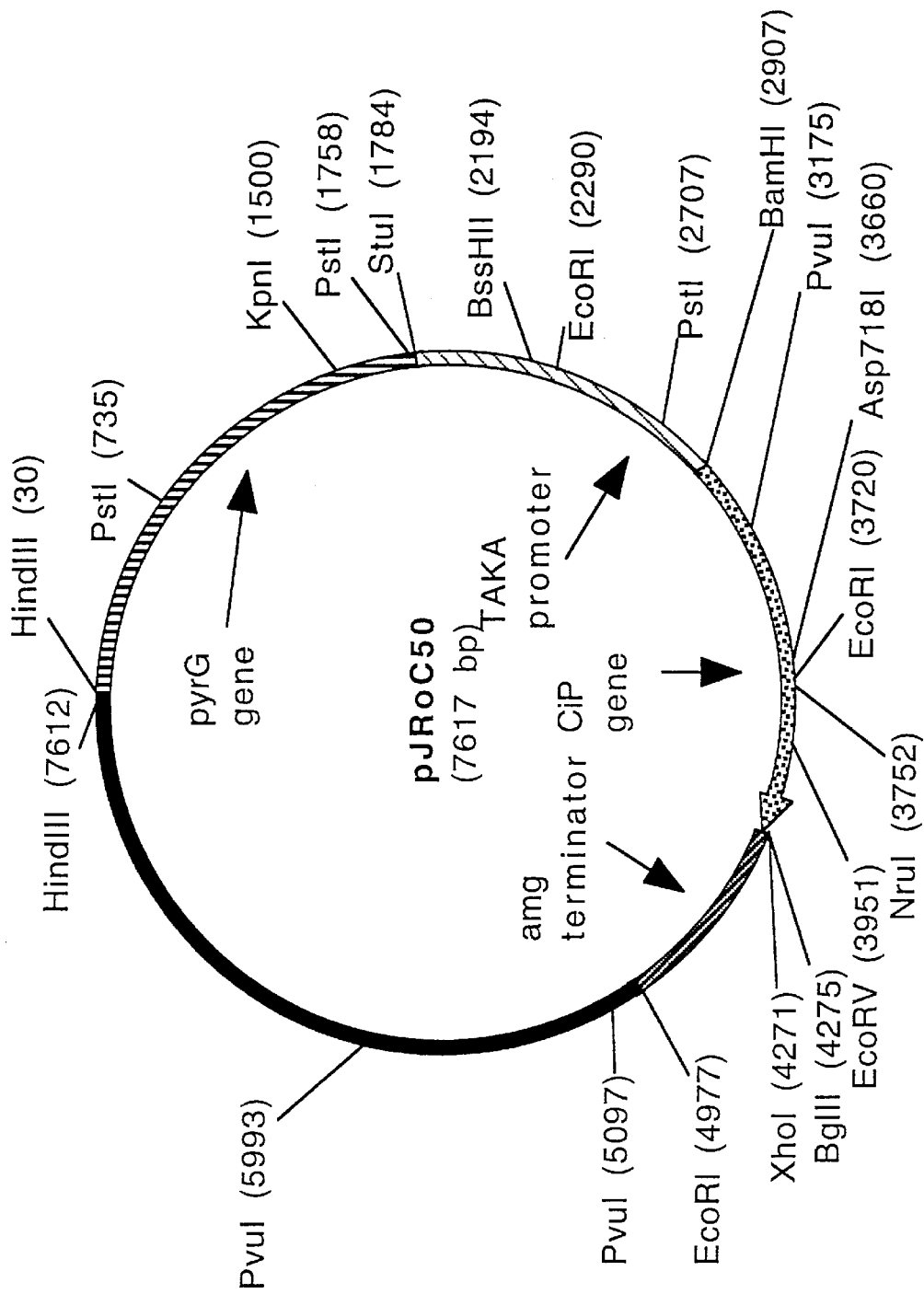
FIG. 7 shows a restriction map of plasmid pJRoC50.

The cDNA encoding the Coprinus cinereus peroxidase was excised from plasmid pJVi9 as a BamHI-XhoI fragment and cloned into plasmid pJeRS6 (FIG. 6) to produce plasmid pJRoC50 (FIG. 7) which contains pyrG as a selectable marker, the TAKA promoter, and the amdS terminator.

Transformants of *Aspergillus oryzae* strain HowB425 were made using 5 µg of purified plasmid pJRoC50 as described below with the following changes. The agar overlay was omitted and the protoplasts were plated directly on Minimal Medium plates. The transformation was conducted with protoplasts at a concentration of 2×10$^7$ protoplasts per ml. One hundred µl of protoplasts were placed on ice with 5 µg DNA for 30 minutes. One ml of SPTC (40% PEG 4000, 0.8M sorbitol, 0.05M Tris pH 8.0, 0.05M CaCl$_2$) was added and the protoplasts were incubated at 34° C. for 20 minutes. The transformation was plated directly onto plates containing Minimal medium. The Minimal medium (pH 6.5) was composed of 6 g of NaNO$_3$, 0.52 g of KCl, 1.52 g of KH$_2$PO$_4$, 1 ml of trace metals, 1 g of glucose, 500 mg of MgSO$_4$—7H$_2$O, 342.3 g of sucrose, and 20 g of Noble agar per liter. The trace metals solution (1000×) was composed of 22 g of ZnSO$_4$—7H$_2$O, 11 g of H$_3$BO$_3$, 5 g of MnCl$_2$—4H$_2$O, 5 g of FeSO$_4$—7H$_2$O, 1.6 g of CoCl$_2$—5H$_2$O, 1.6 g of (NH$_4$)$_6$Mo$_7$O$_{24}$, and 50 g of Na$_4$EDTA per liter. Plates were incubated 5–7 days at 34° C. Transformants were transferred to plates of the same medium and incubated 3–5 days at 37° C.

Sixty-six transformants were assayed for peroxidase activity using the following enzyme assay: 180 µl of substrate buffer {20 ml of 0.1M potassium phosphate-0.01% Tween-80 pH 7.0, 250 µl of 2,2'-azinobis(3-ethylbenzothiazoline-6-sulfonate) (ABTS) solution (22 mg/ml), and 2 µl of 30% hydrogen peroxide} were added to 20 µl of culture supernatant which was diluted 1:900, quickly followed by measurement of the absorbance at 405 nm at 25° C. using a Molecular Devices Thermomax Microplate Reader (Molecular Devices, Sunnyvale, Calif.). Measurements were recorded every 10 seconds over a 2 minute period with mixing and $V_{max}$ values were calculated using the SOFTmax program (Molecular Devices, Sunnyvale, Calif.). The peroxidase units (POXU) per ml were estimated using a standard curve constructed with a known amount of *Cinereus coprinus* peroxidase as a standard. A POXU was defined as the amount of enzyme that catalyzes the conversion of 1.0 µmole per minute of 0.88 mM H$_2$O$_2$, 1.67 mM ABTS, 0.1M phosphate pH 7.0 at 30° C. The four transformants expressing the highest levels were spore purified by streaking spores and picking isolated colonies using the same plates under the same conditions described above.

Final evaluations were performed in shake flasks where approximately 5×10$^6$ spores of each transformant were inoculated into 25 ml of MY25 medium containing 1% yeast extract, 2.5% maltose, 0.2% urea, and 1×MY salts pH 6.5. 1×MY salts was composed of 2 g of MgSO$_4$—7H$_2$O, 2 g of K$_2$PO$_4$, 10 g of KH$_2$PO$_4$, 2 g of citric acid, 0.5 ml of trace metals solution and 1 ml of 10% CaCl$_2$—2H$_2$O per liter. The trace metals solution was composed of 13.9 g of FeSO$_4$—7H$_2$O, 8.5 g of MnSO$_4$—H$_2$O, 14.28 g of ZnSO$_4$—7H$_2$O, 1.63 g of CuSO$_4$, 0.24 g of NiCl$_2$—6H$_2$O, and 3.0 g of citric acid per liter. Hemin was added to a final concentration of 0.01 mg/ml from a fresh 10 mg/ml stock prepared in 50 mM NaOH. The shake flasks were incubated at 34° C. and 200 rpm for 7 to 8 days. The best peroxidase producer was designated JRoC50.3.18A.

Example 7:

Transformation of *Aspergillus oryzae* JRoC50.3.18A with pAJ023

*Aspergillus oryzae* strain JRoC50.3.18A was transformed with pAJ023 in order to determine whether overexpression of the *Aspergillus oryzae* hemB gene increased peroxidase production. As a control, pBANe6 was also used to transform *Aspergillus oryzae* JRoc 50.3.18A.

The transformation was conducted with protoplasts at a concentration of 2×10$^7$ protoplasts per ml. One hundred µl of protoplasts were incubated on ice with 10 µg DNA and 200 µl of 60% PEG 4000-10 mM HEPES-10 mM CaCl$_2$ solution for 30 minutes. One ml of SPTC (40% PEG 4000, 0.8M sorbitol, 0.05M Tris pH 8.0, 0.05M CaCl$_2$) was added and the protoplasts were incubated at 34° C. for 20 minutes. Aliquots of 0.25 ml of the transformation were added to 15 ml of COVE agar overlay (same as COVE media+0.7% low melt agar) prior to plating onto COVE transformation plates (per liter: 0.52 g of KCl, 0.52 g of MgSO$_4$—7H$_2$O, 1.52 g of KH$_2$PO$_4$, 1 ml of trace metals solution as described in Example 6, 342.3 g of sucrose, 25 g of Noble agar, 10 ml of 1M acetamide, and 10 ml of 3M CsCl) for amdS transformations. Plates were incubated 5–7 days at room temperature. Transformants were transferred to plates of the same medium and incubated 3–5 days at 37° C. The transformants were then purified by streaking spores and picking isolated colonies using the same plates under the same conditions.

Example 8:

Peroxidase Production by hemB Primary Transformants

A total of 20 *Aspergillus oryzae* hemB transformants and 42 control transformants (transformants of JRoC 50.3.18A with the *Aspergillus oryzae* expression vector without *Aspergillus oryzae* hemB) were grown in 24 well plates and assayed for peroxidase production as described in Example 6.

The results of the peroxidase assays showed no increase in the number of transformants producing higher levels of peroxidase activity relative to the control transformants.

DEPOSIT OF MICROORGANISMS

The following strain has been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
|---|---|---|
| E. coli DH5α (pAJ007-6) | NRRL B-21564 | April 22, 1996 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A substantially pure porphobilinogen synthase obtained from an Aspergillus strain.

2. The porphobilinogen synthase of claim 1, wherein the synthase is encoded by a nucleic acid sequence capable of hybridizing with a probe which hybridizes to the nucleic acid sequence of SEQ ID NO:1 under conditions of prehybridization and hybridization at 42° C. in 5×SSC, 50 mM sodium phosphate, pH 7.0, 5×Denhardt's solution, 0.1% SDS, 5 mM EDTA, 10 μg/ml denatured salmon sperm DNA, and 50% formamide, followed by washing at 0.1 ×SSC, 0.1% SDS for 15 minutes at 42° C.

3. The porphobilinogen synthase of claim 1 obtained from an *Aspergillus oryzae* strain.

4. The porphobilinogen synthase of claim 3 obtained from *Aspergillus oryzae* IFO 4177 or a mutant strain thereof which retains all the identifying characteristics of IFO 4177.

5. The porphobilinogen synthase of claim 1, wherein the synthase comprises the amino acid sequence of SEQ ID NO:2.

6. The porphobilinogen synthase of claim 1, wherein the synthase comprises an amino acid sequence which differs by 1–3 amino acids from the amino acid sequence of SEQ ID NO:2.

7. The porphobilinogen synthase of claim 6, wherein the synthase comprises an amino acid sequence which differs by three amino acids from the amino acid sequence of SEQ ID NO:2.

8. The porphobilinogen synthase of claim 6, wherein the synthase comprises an amino acid sequence which differs by two amino acids from the amino acid sequence of SEQ ID NO:2.

9. The porphobilinogen synthase of claim 6, wherein the synthase comprises an amino acid sequence which differs by one amino acids from the amino acid sequence of SEQ ID NO:2.

* * * * *

UNITED STATES PATENT AND TRADEMARK OFFICE
CERTIFICATE OF CORRECTION

PATENT NO. : 5,866,391
DATED : February 2, 1999
INVENTOR(S) : Jones et al.

It is certified that error appears in the above-identified patent and that said Letters Patent is hereby corrected as shown below:

Col. 11, line 9: after "Wetmur et al.", delete "15"
Col. 11, line 51: delete "5'-GCATATTTAAATGATGTCCTTTTCTAATCTCGT-3'" and insert --5'-GCA__TATTTAAAT__GATGTCCTTTTCTAATCTCGT-3'--
Col. 11, line 54: delete "5'- ATATTAATTAATCCATCTAGCTAAATCATT-3'" and insert --5'- ATA__TTAATTAA__TCCATCTAGCTAAATCATT-3'--

Signed and Sealed this

Twenty-eighth Day of December, 1999

Q. TODD DICKINSON

Attest:

Attesting Officer     Acting Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1807 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CTGGACCAAT  GGTAACCCTC  CGTAATTGCC  TTACAGATTT  AGCCCAGGGG  GGTTATGGTA      60
TCCTTGGGTA  TTGAGGCCTG  GAAATTTTTT  TAGCCACCAG  TTTACAGCCA  GTTTCCGTTT     120
GTAAATATTT  CACATCCCCC  GACCCTGTCC  CAATACAATA  ATTTTTTCGC  TATATATAAC     180
GCCCCTAGCG  TTGTTTTATG  ATCCTTAAAT  CCTTACTTGT  ACCTGAAAAT  TGCAACAAAT     240
GTACTGACCT  GGATCGCTGG  CCATTTATAT  CATTGCCCTG  CGAAGTCGTA  TTCTGCCAGT     300
GGCACAGGCG  CTATTCTCTT  TTCTTCCCTC  CACCGCGTTT  CTATCTTCCA  TAGCACCCCA     360
CTTGCTTGCC  GCTCCTGTCA  TTATGTCCTT  TTCTAATCTC  GTCTCTGACC  TCGCCTTCAG     420
AGATTCTCAT  GATGACCGAA  GTTCTCAGAT  ATCTCAGGTA  CAATCGCAAG  CCACTGCACG     480
ATCGTATACA  AGCACAGCTG  CCACAAGCGT  CAGCATATCT  GGCGACATCT  CAAGCCAGCT     540
TCATTCCGGT  TACAGCCATC  CACTGAGCCG  ATCATGGCAG  GCTGAAAGAC  AGTTGACTAA     600
AGTCCGCATT  TTCTTTTGTA  TTTACTGAGC  TGCTCTAACC  CCGAGATAGG  AAATGCTTAT     660
TTATCCTCTC  TTCATCACCG  ATAATCCCGA  TGAGGAGACT  CCTATCCCGT  CTCTCCCTGG     720
ACAGTATCGT  CGAGGATTAA  ACCGTCTAGT  TCCTTTCATC  AAACCACTTG  CCCACAAGGG     780
GCTACGCTCA  GTCATCCTGT  TTGGCGTCCC  ACTACACCCC  TCTGCGAAGG  ATGCACTAGG     840
TACCGCTGCA  GACGATCCAT  CTGGACCGGT  AATTCAAGCT  ATTCGCTTGC  TTAGGTCGCG     900
GTTTCCTCAA  CTTTATATCG  TGACAGATGT  GTGCCTTTGC  GAGTATACTT  CGCATGGCCA     960
CTGTGGGATA  CTGCGAGAAG  ATGGGACTCT  TGATAATACA  CAGTCTGTGG  ATCGGATTTC    1020
GGATGTTGCT  CTGGCTTATG  CTGCCGCCGG  AGCCCATTGT  GTCGCTCCGT  CTGATATGAA    1080
TGATGGGCGA  GTGCGTGCTA  TAAAACTGAA  GCTTATTGAA  GCCGGGATGG  CCCACCGTGT    1140
CCTACTGATG  TCCTACAGCG  CCAAATTTAG  CGGTTGTTTG  TACGGCCCTT  TCCGTGATGC    1200
```

-continued

```
AGCGGGGTCC TGCCCATCAT TCGGGGATCG CAGATGCTAC CAGTTACCAC CCGGAGGCCG    1260

TGGACTTGCT CGGCGCGCTA TACAGAGAGA TATAGGCGAA GGGGCAGACA TCATAATGGT    1320

AAAGCCGGCG AGCAGCTACC TGGACATTAT CAGAGACGCA AAAGAAATTG CCAAAGACAT    1380

TCCCATTGCT GCTTACCAGG TCAGCGGTGA GTATGCTATG ATACATGCTG GTGCCAAGGC    1440

GGGCGTATTT GACTTGAAAT CCATGGCCTT TGAAAGTACT GAAGGGATTA TAAGGGCTGG    1500

TGCTGGGATT ATAGTAAGCT ATTTCGTGCC TGATTTTCTA GATTGGCTTT CGAAATGATT    1560

TAGCTAGATG GAGCGTGATG AAAGCATCCA CCAGATAAAT AGCAGTGACG ATCGCGTTTG    1620

AATCATACCT ATTGGAGTAG AAGTCTCGGT ATCTCGTTGG GGATTCTCTA GGTTGCTTAT    1680

TTAACGTAAT GCCACGCCAT GTGTTATATA TTGCCTAAAT ACTTTTATAA AAGATACACC    1740

AAGCTGATGG TGCCAAGTGA CCACTTCTAA TAAATACAAT TATACCAATT CCTCCGAAAT    1800

ATGCGGG                                                              1807
```

( 2 ) INFORMATION FOR SEQ ID NO:2:

( i ) SEQUENCE CHARACTERISTICS:
        ( A ) LENGTH: 375 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met  Ser  Phe  Ser  Asn  Leu  Val  Ser  Asp  Leu  Ala  Phe  Arg  Asp  Ser  His
 1              5                        10                       15

Asp  Asp  Arg  Ser  Ser  Gln  Ile  Ser  Gln  Val  Gln  Ser  Gln  Ala  Thr  Ala
              20                       25                       30

Arg  Ser  Tyr  Thr  Ser  Thr  Ala  Ala  Thr  Ser  Val  Ser  Ile  Ser  Gly  Asp
                   35                       40                       45

Ile  Ser  Ser  Gln  Leu  His  Ser  Gly  Tyr  Ser  His  Pro  Leu  Ser  Arg  Ser
         50                       55                       60

Trp  Gln  Ala  Glu  Arg  Gln  Leu  Thr  Lys  Glu  Met  Leu  Ile  Tyr  Pro  Leu
65                        70                       75                       80

Phe  Ile  Thr  Asp  Asn  Pro  Asp  Glu  Glu  Thr  Pro  Ile  Pro  Ser  Leu  Pro
                        85                       90                       95

Gly  Gln  Tyr  Arg  Arg  Gly  Leu  Asn  Arg  Leu  Val  Pro  Phe  Ile  Lys  Pro
                   100                      105                      110

Leu  Ala  His  Lys  Gly  Leu  Arg  Ser  Val  Ile  Leu  Phe  Gly  Val  Pro  Leu
              115                      120                      125

His  Pro  Ser  Ala  Lys  Asp  Ala  Leu  Gly  Thr  Ala  Ala  Asp  Asp  Pro  Ser
         130                      135                      140

Gly  Pro  Val  Ile  Gln  Ala  Ile  Arg  Leu  Leu  Arg  Ser  Arg  Phe  Pro  Gln
145                      150                      155                      160

Leu  Tyr  Ile  Val  Thr  Asp  Val  Cys  Leu  Cys  Glu  Tyr  Thr  Ser  His  Gly
                        165                      170                      175

His  Cys  Gly  Ile  Leu  Arg  Glu  Asp  Gly  Thr  Leu  Asp  Asn  Thr  Gln  Ser
                   180                      185                      190

Val  Asp  Arg  Ile  Ser  Asp  Val  Ala  Leu  Ala  Tyr  Ala  Ala  Ala  Gly  Ala
              195                      200                      205

His  Cys  Val  Ala  Pro  Ser  Asp  Met  Asn  Asp  Gly  Arg  Val  Arg  Ala  Ile
         210                      215                      220
```

| | | | | | | | | | | | | | | |
|---|---|---|---|---|---|---|---|---|---|---|---|---|---|---|
| Lys 225 | Leu | Lys | Leu | Ile | Glu 230 | Ala | Gly | Met | Ala | His 235 | Arg | Val | Leu | Leu Met 240 |
| Ser | Tyr | Ser | Ala | Lys 245 | Phe | Ser | Gly | Cys | Leu 250 | Tyr | Gly | Pro | Phe | Arg Asp 255 |
| Ala | Ala | Gly | Ser 260 | Cys | Pro | Ser | Phe | Gly 265 | Asp | Arg | Arg | Cys | Tyr 270 | Gln Leu |
| Pro | Pro | Gly 275 | Gly | Arg | Gly | Leu | Ala 280 | Arg | Arg | Ala | Ile | Gln 285 | Arg | Asp Ile |
| Gly | Glu 290 | Gly | Ala | Asp | Ile | Ile 295 | Met | Val | Lys | Pro | Ala 300 | Ser | Ser | Tyr Leu |
| Asp 305 | Ile | Ile | Arg | Asp | Ala 310 | Lys | Glu | Ile | Ala | Lys 315 | Asp | Ile | Pro | Ile Ala 320 |
| Ala | Tyr | Gln | Val | Ser 325 | Gly | Glu | Tyr | Ala | Met 330 | Ile | His | Ala | Gly | Ala Lys 335 |
| Ala | Gly | Val | Phe 340 | Asp | Leu | Lys | Ser | Met 345 | Ala | Phe | Glu | Ser | Thr 350 | Glu Gly |
| Ile | Ile | Arg 355 | Ala | Gly | Ala | Gly | Ile 360 | Ile | Val | Ser | Tyr | Phe 365 | Val | Pro Asp |
| Phe | Leu 370 | Asp | Trp | Leu | Ser | Lys 375 | | | | | | | | |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GTNGCNCCNW SNGAYATGAT GGA        23

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCRTCNCGTR AANCCRTA        18

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTGGCTCCGA GTGATAT        17

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GCATCGCGAA AAGGACCG    18

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

GCATATTTAA ATGATGTCCT TTTCTAATCT CGT    33

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

ATATTAATTA ATCCATCTAG CTAAATCATT    30

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

GCGCGAATTC GTNGGNATNG GNATNAAYCA YGG    33

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

GCGGATCCGG NGGRCARTTN GACAT    25

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:11:

GCGAATTCAC NCCNCARGTN TTYGAYAC    28

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:12:

GCGGATCCRA AYTCNCCNGG RAANGG    26

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
GCGCGAATTC TGGCARTCNA C                                              21
```

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
GCGCGAATTC TGGCARAGNA TG                                             22
```

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
GGATCCGACA TYTTNGCCAT NGC                                            23
```

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
GTYTCRATRT AGAAYTG                                                   17
```

( 2 ) INFORMATION FOR SEQ ID NO:17:

( i ) SEQUENCE CHARACTERISTICS:
        ( A ) LENGTH: 342 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:17:

```
Met His Thr Ala Glu Phe Leu Glu Thr Glu Pro Thr Glu Ile Ser Ser
  1               5                  10                  15

Val Leu Ala Gly Gly Tyr Asn His Pro Leu Leu Arg Gln Trp Gln Ser
             20                  25                  30

Glu Arg Gln Leu Thr Lys Asn Met Leu Ile Phe Pro Leu Phe Ile Ser
         35                  40                  45

Asp Asn Pro Asp Asp Phe Thr Glu Ile Asp Ser Leu Pro Asn Ile Asn
         50                  55                  60

Arg Ile Gly Val Asn Arg Leu Lys Asp Tyr Leu Lys Pro Leu Val Ala
```

| | | | | 65 | | | | | 70 | | | | | 75 | | | | | 80 |
|---|---|---|---|---|---|---|---|---|---|---|---|---|---|---|---|---|---|---|---|
| Lys | Gly | Leu | Arg | Ser | Val | Ile | Leu | Phe | Gly | Val | Pro | Leu | Ile | Pro | Gly |
| | | | | 85 | | | | | 90 | | | | | 95 | |
| Thr | Lys | Asp | Pro | Val | Gly | Thr | Ala | Ala | Asp | Asp | Pro | Ala | Gly | Pro | Val |
| | | | 100 | | | | | 105 | | | | | 110 | | |
| Ile | Gln | Gly | Ile | Lys | Phe | Ile | Arg | Glu | Tyr | Phe | Pro | Glu | Leu | Tyr | Ile |
| | | | 115 | | | | | 120 | | | | | 125 | | |
| Ile | Cys | Asp | Val | Cys | Leu | Cys | Glu | Tyr | Thr | Ser | His | Gly | His | Cys | Gly |
| | | 130 | | | | | 135 | | | | | 140 | | | |
| Val | Leu | Tyr | Asp | Asp | Gly | Thr | Ile | Asn | Arg | Glu | Arg | Ser | Val | Ser | Arg |
| 145 | | | | | | 150 | | | | | 155 | | | | 160 |
| Leu | Ala | Ala | Val | Ala | Val | Asn | Tyr | Ala | Lys | Ala | Gly | Ala | His | Cys | Val |
| | | | | 165 | | | | | 170 | | | | | 175 | |
| Ala | Pro | Ser | Asp | Met | Ile | Asp | Gly | Arg | Ile | Arg | Asp | Ile | Lys | Arg | Gly |
| | | | 180 | | | | | 185 | | | | | 190 | | |
| Leu | Ile | Asn | Ala | Asn | Leu | Ala | His | Lys | Thr | Phe | Val | Leu | Ser | Tyr | Ala |
| | | | 195 | | | | | 200 | | | | | 205 | | |
| Ala | Lys | Phe | Ser | Gly | Asn | Leu | Tyr | Gly | Pro | Phe | Arg | Asp | Ala | Ala | Cys |
| | | 210 | | | | | 215 | | | | | 220 | | | |
| Ser | Ala | Pro | Ser | Asn | Gly | Asp | Arg | Lys | Cys | Tyr | Gln | Leu | Pro | Pro | Ala |
| 225 | | | | | | 230 | | | | | 235 | | | | 240 |
| Gly | Arg | Gly | Leu | Ala | Arg | Arg | Ala | Leu | Glu | Arg | Asp | Met | Ser | Glu | Gly |
| | | | | 245 | | | | | 250 | | | | | 255 | |
| Ala | Asp | Gly | Ile | Ile | Val | Lys | Pro | Ser | Thr | Phe | Tyr | Leu | Asp | Ile | Met |
| | | | 260 | | | | | 265 | | | | | 270 | | |
| Arg | Asp | Ala | Ser | Glu | Ile | Cys | Lys | Asp | Leu | Pro | Ile | Cys | Ala | Tyr | His |
| | | | 275 | | | | | 280 | | | | | 285 | | |
| Val | Ser | Asp | Glu | Tyr | Ala | Met | Leu | His | Ala | Ala | Ala | Glu | Lys | Gly | Val |
| | | | 290 | | | | | 295 | | | | | 300 | | |
| Val | Asp | Leu | Lys | Thr | Ile | Ala | Phe | Glu | Ser | His | Gln | Gly | Phe | Leu | Arg |
| 305 | | | | | | 310 | | | | | 315 | | | | 320 |
| Ala | Gly | Ala | Arg | Leu | Ile | Ile | Thr | Tyr | Leu | Ala | Pro | Glu | Phe | Leu | Asp |
| | | | | 325 | | | | | 330 | | | | | 335 | |
| Trp | Leu | Asp | Glu | Glu | Asn | | | | | | | | | | |
| | | | 340 | | | | | | | | | | | | |

( 2 ) INFORMATION FOR SEQ ID NO:18:

( i ) SEQUENCE CHARACTERISTICS:
        ( A ) LENGTH: 330 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:18:

| Met | Gln | Pro | Gln | Ser | Val | Leu | His | Ser | Gly | Tyr | Phe | His | Pro | Leu | Leu |
|---|---|---|---|---|---|---|---|---|---|---|---|---|---|---|---|
| 1 | | | | 5 | | | | | 10 | | | | | 15 | |
| Arg | Ala | Trp | Gln | Thr | Ala | Thr | Thr | Leu | Asn | Ala | Ser | Asn | Leu | Ile |
| | | | 20 | | | | | 25 | | | | | 30 | | |
| Tyr | Pro | Ile | Phe | Val | Thr | Asp | Val | Pro | Asp | Asp | Ile | Gln | Pro | Ile | Thr |
| | | | 35 | | | | | 40 | | | | | 45 | | |
| Ser | Leu | Pro | Gly | Val | Ala | Arg | Tyr | Gly | Val | Lys | Arg | Leu | Glu | Glu | Met |
| | | 50 | | | | | 55 | | | | | 60 | | | |
| Leu | Arg | Pro | Leu | Val | Glu | Glu | Gly | Leu | Arg | Cys | Val | Leu | Ile | Phe | Gly |
| 65 | | | | | | 70 | | | | | 75 | | | | 80 |

| Val | Pro | Ser | Arg | Val | Pro | Lys | Asp | Glu | Arg | Gly | Ser | Ala | Ala | Asp | Ser |
|---|---|---|---|---|---|---|---|---|---|---|---|---|---|---|---|
| | | | | 85 | | | | 90 | | | | | | 95 | |

Glu Glu Ser Pro Ala Ile Glu Ala Ile His Leu Leu Arg Lys Thr Phe
            100              105                110

Pro Asn Leu Leu Val Ala Cys Asp Val Cys Leu Cys Pro Tyr Thr Ser
        115              120                125

His Gly His Cys Gly Leu Leu Ser Glu Asn Gly Ala Phe Arg Ala Glu
    130              135              140

Glu Ser Arg Gln Arg Leu Ala Glu Val Ala Leu Ala Tyr Ala Lys Ala
145              150              155              160

Gly Cys Gln Val Val Ala Pro Ser Asp Met Met Asp Gly Arg Val Glu
            165              170              175

Ala Ile Lys Glu Ala Leu Met Ala His Gly Leu Gly Asn Arg Val Ser
        180              185              190

Val Met Ser Tyr Ser Ala Lys Phe Ala Ser Cys Phe Tyr Gly Pro Phe
        195              200              205

Arg Asp Ala Ala Lys Ser Ser Pro Ala Phe Gly Asp Arg Arg Cys Tyr
        210              215              220

Gln Leu Pro Pro Gly Ala Arg Gly Leu Ala Leu Arg Ala Val Asp Arg
225              230              235              240

Asp Val Arg Glu Gly Ala Asp Met Leu Met Val Lys Pro Gly Met Pro
                245              250              255

Tyr Leu Asp Ile Val Arg Glu Val Lys Asp Lys His Pro Asp Leu Pro
            260              265              270

Leu Ala Val Tyr His Val Ser Gly Glu Phe Ala Met Leu Trp His Gly
        275              280              285

Ala Gln Ala Gly Ala Phe Asp Leu Lys Ala Ala Val Leu Glu Ala Met
    290              295              300

Thr Ala Phe Arg Arg Ala Gly Ala Asp Ile Ile Ile Thr Tyr Tyr Thr
305              310              315              320

Pro Gln Leu Leu Gln Trp Leu Lys Glu Glu
            325              330

(2) INFORMATION FOR SEQ ID NO:19:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

Met His His Gln Ser Val Leu His Ser Gly Tyr Phe His Pro Leu Leu
1                5              10              15

Arg Ala Trp Gln Thr Thr Pro Ser Thr Val Ser Ala Thr Asn Leu Ile
            20              25              30

Tyr Pro Ile Phe Val Thr Asp Val Pro Asp Asp Val Gln Pro Ile Ala
        35              40              45

Ser Leu Pro Gly Val Ala Arg Tyr Gly Val Asn Gln Leu Glu Glu Met
    50              55              60

Leu Arg Pro Leu Val Glu Ala Gly Leu Arg Cys Val Leu Ile Phe Gly
65              70              75              80

Val Pro Ser Arg Val Pro Lys Asp Glu Gln Gly Ser Ala Ala Asp Ser
            85              90              95

| | | | | | | | | | | | | | | |
|---|---|---|---|---|---|---|---|---|---|---|---|---|---|---|
|Glu|Asp|Ser|Pro 100|Thr|Ile|Glu|Ala|Val 105|Arg|Leu|Leu|Arg|Lys 110|Thr|Phe|
|Pro|Thr|Leu 115|Leu|Val|Ala|Cys|Asp 120|Val|Cys|Leu|Cys|Pro 125|Tyr|Thr|Ser|
|His|Gly 130|His|Cys|Gly|Leu|Leu 135|Ser|Glu|Asn|Gly|Ala 140|Phe|Leu|Ala|Glu|
|Glu 145|Ser|Arg|Gln|Arg|Leu 150|Ala|Glu|Val|Ala|Leu 155|Ala|Tyr|Ala|Lys|Ala 160|
|Gly|Cys|Gln|Val|Val 165|Ala|Pro|Ser|Asp|Met 170|Met|Asp|Gly|Arg|Val 175|Glu|
|Ala|Ile|Lys|Ala 180|Ala|Leu|Leu|Lys|His 185|Gly|Leu|Gly|Asn|Arg 190|Val|Ser|
|Val|Met|Ser 195|Tyr|Ser|Ala|Lys|Phe 200|Ala|Ser|Cys|Phe|Tyr 205|Gly|Pro|Phe|
|Arg|Asp 210|Ala|Ala|Gln|Ser|Ser 215|Pro|Ala|Phe|Gly|Asp 220|Arg|Arg|Cys|Tyr|
|Gln 225|Leu|Pro|Pro|Gly|Ala 230|Arg|Gly|Leu|Ala|Leu 235|Arg|Ala|Val|Ala|Arg 240|
|Asp|Ile|Gln|Glu|Gly 245|Ala|Asp|Ile|Leu|Met 250|Val|Lys|Pro|Gly|Leu 255|Pro|
|Tyr|Leu|Asp|Met 260|Val|Gln|Glu|Val|Lys 265|Asp|Lys|His|Pro|Glu 270|Leu|Pro|
|Leu|Ala|Val 275|Tyr|Gln|Val|Ser|Gly 280|Glu|Phe|Ala|Met|Leu 285|Trp|His|Gly|
|Ala|Lys 290|Ala|Gly|Ala|Phe|Asp 295|Leu|Arg|Thr|Ala|Val 300|Leu|Glu|Ser|Met|
|Thr 305|Ala|Phe|Arg|Arg|Ala 310|Gly|Ala|Asp|Ile|Ile 315|Ile|Thr|Tyr|Phe|Ala 320|
|Pro|Gln|Leu|Leu|Lys 325|Trp|Leu|Lys|Glu|Glu 330| | | | | | |

( 2 ) INFORMATION FOR SEQ ID NO:20:

( i ) SEQUENCE CHARACTERISTICS:
        ( A ) LENGTH: 323 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:20:

| | | | | | | | | | | | | | | |
|---|---|---|---|---|---|---|---|---|---|---|---|---|---|---|
|Thr 1|Asp|Leu|Ile|Gln 5|Arg|Pro|Arg|Arg|Leu 10|Arg|Lys|Ser|Pro|Ala 15|Leu|
|Pro|Arg|Met|Phe 20|Glu|Glu|Thr|Thr|Leu 25|Ser|Leu|Asn|Asp|Leu 30|Val|Leu|
|Pro|Ile|Phe 35|Val|Glu|Glu|Glu|Ile 40|Asp|Asp|Tyr|Lys|Ala 45|Val|Glu|Ala|
|Met|Pro 50|Gly|Val|Met|Arg|Ile 55|Pro|Glu|Lys|His|Leu 60|Ala|Arg|Glu|Ile|
|Glu 65|Arg|Ile|Ala|Asn|Ala 70|Gly|Ile|Arg|Ser|Val 75|Met|Thr|Phe|Gly|Ile 80|
|Ser|His|His|Thr|Asp 85|Glu|Thr|Gly|Glu|Arg 90|Ala|Trp|Arg|Glu|Asp 95|Gly|
|Leu|Val|Ala|Arg 100|Met|Ser|Arg|Ile|Cys 105|Lys|Gln|Thr|Val|Pro 110|Glu|Met|
|Ile|Val|Met|Ser|Asp|Thr|Cys|Phe|Cys|Glu|Tyr|Thr|Ser|His|Gly|His|

|     |     |     | 115 |     |     |     | 120 |     |     |     | 125 |     |     |     |
|-----|-----|-----|-----|-----|-----|-----|-----|-----|-----|-----|-----|-----|-----|-----|
| Cys | Gly | Val | Leu | Cys | Glu | His | Gly | Val | Asp | Asn | Asp | Ala | Thr | Leu | Glu |
| 130 |     |     |     |     |     | 135 |     |     |     | 140 |     |     |     |     |

Cys Gly Val Leu Cys Glu His Gly Val Asp Asn Asp Ala Thr Leu Glu
130                      135                140

Asn Leu Gly Lys Gln Ala Val Ala Ala Ala Ala Gly Ala Asp Phe
145                  150                155                160

Ile Ala Pro Ser Ala Ala Met Asp Gly Gln Val Gln Ala Ile Arg Gln
                165              170                175

Ala Leu Asp Ala Ala Gly Phe Lys Asp Thr Ala Ile Met Ser Tyr Ser
                180              185                190

Thr Lys Phe Ala Ser Ser Phe Tyr Gly Pro Phe Arg Glu Ala Ala Gly
            195              200              205

Ser Ala Leu Lys Gly Asp Arg Lys Ser Tyr Gln Met Asn Pro Met Asn
    210                  215              220

Arg Ala Glu Gly Ile Ala Glu Tyr Leu Leu Asp Glu Ala Gln Gly Ala
225                  230              235                240

Asp Cys Leu Met Val Lys Pro Ala Gly Ala Tyr Leu Asp Ile Val Arg
                245              250                255

Glu Leu Arg Glu Arg Thr Glu Leu Pro Ile Gly Ala Tyr Gln Val Ser
            260              265              270

Gly Glu Tyr Ala Met Ile Lys Phe Ala Ala Leu Ala Gly Ala Ile Asp
            275              280              285

Glu Glu Lys Val Val Leu Glu Ser Leu Gly Ser Ile Lys Arg Ala Gly
        290              295              300

Ala Asp Leu Ile Phe Ser Tyr Phe Ala Leu Asp Leu Ala Glu Lys Lys
305                  310              315                320

Ile Leu Arg ( 2 ) INFORMATION FOR SEQ ID NO:21:

( i ) SEQUENCE CHARACTERISTICS:
        ( A ) LENGTH: 398 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:21:

His Thr Phe Val Asp Leu Lys Ser Pro Phe Thr Leu Ser Asn Tyr Leu
1               5                  10                 15

Ser Phe Ser Ser Ser Lys Arg Arg Gln Pro Pro Ser Leu Phe Thr Val
            20                  25                  30

Arg Ala Ser Asp Ser Asp Phe Glu Ala Ala Val Val Ala Gly Lys Val
            35              40                  45

Pro Glu Ala Pro Pro Val Pro Pro Thr Pro Ala Ser Pro Ala Gly Thr
    50                  55                  60

Pro Val Val Pro Ser Leu Pro Ile Gln Arg Arg Pro Arg Arg Asn Arg
65                  70                  75                  80

Arg Ser Pro Ala Leu Arg Ser Ala Phe Gln Glu Thr Thr Leu Ser Pro
                85                  90                  95

Ala Asn Phe Val Tyr Pro Leu Phe Ile His Glu Gly Glu Glu Asp Thr
            100                 105                 110

Pro Ile Gly Ala Met Pro Gly Cys Tyr Arg Leu Gly Trp Arg His Gly
            115                 120                 125

Leu Leu Glu Glu Val Ala Lys Ala Arg Asp Val Gly Val Asn Ser Val
130                 135                 140

| | | | | | | | | | | | | | | | |
|---|---|---|---|---|---|---|---|---|---|---|---|---|---|---|---|
| Val | Leu | Phe | Pro | Lys | Ile | Pro | Asp | Ala | Leu | Lys | Thr | Pro | Thr | Gly | Asp |
| 145 | | | | 150 | | | | | 155 | | | | | | 160 |
| Glu | Ala | Tyr | Asn | Glu | Asp | Gly | Leu | Val | Pro | Arg | Ser | Ile | Arg | Leu | Leu |
| | | | | 165 | | | | | 170 | | | | | 175 | |
| Lys | Asp | Lys | Tyr | Pro | Asp | Leu | Ile | Ile | Tyr | Thr | Asp | Val | Ala | Leu | Asp |
| | | | 180 | | | | | 185 | | | | | 190 | | |
| Pro | Tyr | Ser | Ser | Asp | Gly | His | Asp | Gly | Ile | Val | Arg | Glu | Asp | Gly | Val |
| | | | 195 | | | | 200 | | | | | 205 | | | |
| Ile | Met | Asn | Asp | Glu | Thr | Val | His | Gln | Leu | Cys | Lys | Gln | Ala | Val | Ala |
| | 210 | | | | | 215 | | | | | 220 | | | | |
| Gln | Ala | Arg | Ala | Gly | Ala | Asp | Val | Val | Ser | Pro | Ser | Asp | Met | Met | Asp |
| 225 | | | | | 230 | | | | | 235 | | | | | 240 |
| Gly | Arg | Val | Gly | Ala | Met | Arg | Val | Ala | Leu | Asp | Ala | Glu | Gly | Phe | Gln |
| | | | | 245 | | | | | 250 | | | | | 255 | |
| His | Val | Ser | Ile | Met | Ser | Tyr | Thr | Ala | Lys | Tyr | Ala | Ser | Ser | Phe | Tyr |
| | | | 260 | | | | | 265 | | | | | 270 | | |
| Gly | Pro | Phe | Arg | Glu | Ala | Leu | Asp | Ser | Asn | Pro | Arg | Phe | Gly | Asp | Lys |
| | | 275 | | | | | 280 | | | | | 285 | | | |
| Lys | Thr | Tyr | Gln | Met | Asn | Pro | Ala | Asn | Tyr | Arg | Glu | Ala | Leu | Thr | Glu |
| | 290 | | | | | 295 | | | | | 300 | | | | |
| Met | Arg | Glu | Asp | Glu | Ser | Glu | Gly | Ala | Asp | Ile | Leu | Leu | Val | Lys | Pro |
| 305 | | | | | 310 | | | | | 315 | | | | | 320 |
| Gly | Leu | Pro | Tyr | Leu | Asp | Ile | Ile | Arg | Leu | Leu | Arg | Asp | Asn | Ser | Pro |
| | | | | 325 | | | | | 330 | | | | | 335 | |
| Leu | Pro | Ile | Ala | Ala | Tyr | Gln | Val | Ser | Gly | Glu | Tyr | Ser | Met | Ile | Lys |
| | | | 340 | | | | | 345 | | | | | 350 | | |
| Ala | Gly | Gly | Ala | Leu | Lys | Met | Ile | Asp | Glu | Glu | Lys | Val | Met | Met | Glu |
| | | 355 | | | | | 360 | | | | | 365 | | | |
| Ser | Leu | Leu | Cys | Leu | Arg | Arg | Ala | Gly | Ala | Asp | Ile | Ile | Leu | Thr | Tyr |
| | 370 | | | | | 375 | | | | | 380 | | | | |
| Phe | Ala | Leu | Gln | Ala | Ala | Arg | Thr | Leu | Cys | Gly | Glu | Lys | Arg | | |
| 385 | | | | | 390 | | | | | 395 | | | | | |

( 2 ) INFORMATION FOR SEQ ID NO:22:

( i ) SEQUENCE CHARACTERISTICS:
        ( A ) LENGTH: 323 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:22:

| | | | | | | | | | | | | | | | |
|---|---|---|---|---|---|---|---|---|---|---|---|---|---|---|---|
| Met | Ser | Gln | Ser | Phe | Asn | Arg | His | Arg | Arg | Leu | Arg | Thr | Ser | Lys | Ala |
| 1 | | | | 5 | | | | | 10 | | | | | 15 | |
| Met | Arg | Glu | Met | Val | Lys | Glu | Thr | Arg | Leu | His | Pro | Ser | Asp | Phe | Ile |
| | | | 20 | | | | | 25 | | | | | 30 | | |
| Tyr | Pro | Ile | Phe | Val | Val | Glu | Gly | Leu | Glu | Gly | Lys | Lys | Ala | Val | Pro |
| | | | 35 | | | | | 40 | | | | | 45 | | |
| Ser | Met | Pro | Asp | Val | His | His | Val | Ser | Leu | Asp | Leu | Leu | Lys | Asp | Glu |
| | 50 | | | | | 55 | | | | | 60 | | | | |
| Val | Ala | Glu | Leu | Val | Lys | Leu | Gly | Ile | Gln | Ser | Val | Ile | Val | Phe | Gly |
| 65 | | | | | 70 | | | | | 75 | | | | | 80 |
| Ile | Pro | Glu | Glu | Lys | Asp | Asp | Cys | Gly | Thr | Gln | Ala | Tyr | His | Asp | His |
| | | | | 85 | | | | | 90 | | | | | 95 | |
| Gly | Ile | Val | Gln | Lys | Ala | Ile | Thr | Glu | Ile | Lys | Glu | His | Phe | Pro | Glu |

-continued

|     |     |     |     |     | 100 |     |     |     |     | 105 |     |     |     |     | 110 |     |
| --- | --- | --- | --- | --- | --- | --- | --- | --- | --- | --- | --- | --- | --- | --- | --- | --- |
| Met | Val | Val | Ala | Asp | Thr | Cys | Leu | Cys | Glu | Tyr | Thr | Asp | His | Gly |
|     |     | 115 |     |     |     | 120 |     |     |     |     | 125 |     |     |     |
| His | Cys | Gly | Leu | Val | Lys | Asp | Gly | Val | Ile | Leu | Asn | Asp | Glu | Ser | Leu |
|     | 130 |     |     |     | 135 |     |     |     |     | 140 |     |     |     |
| Glu | Leu | Leu | Ala | Gln | Thr | Ala | Val | Ser | Gln | Ala | Lys | Ala | Gly | Ala | Asp |
| 145 |     |     |     | 150 |     |     |     | 155 |     |     |     |     | 160 |
| Ile | Ile | Ala | Pro | Ser | Asn | Met | Met | Asp | Gly | Phe | Val | Thr | Val | Ile | Arg |
|     |     |     |     | 165 |     |     |     | 170 |     |     |     |     | 175 |
| Glu | Ala | Leu | Asp | Lys | Glu | Gly | Phe | Val | Asn | Ile | Pro | Ile | Met | Ser | Tyr |
|     |     |     | 180 |     |     |     | 185 |     |     |     | 190 |     |
| Ala | Val | Lys | Tyr | Ser | Ser | Glu | Phe | Tyr | Gly | Pro | Phe | Arg | Asp | Ala | Ala |
|     |     | 195 |     |     |     | 200 |     |     |     | 205 |     |     |
| Asn | Ser | Thr | Pro | Gln | Phe | Gly | Asp | Arg | Lys | Thr | Tyr | Gln | Met | Asp | Pro |
|     | 210 |     |     |     | 215 |     |     |     | 220 |     |     |     |
| Ala | Asn | Arg | Met | Glu | Ala | Leu | Arg | Glu | Ala | Gln | Ser | Asp | Val | Glu | Glu |
| 225 |     |     |     | 230 |     |     |     | 235 |     |     |     | 240 |
| Gly | Ala | Asp | Phe | Leu | Ile | Val | Lys | Pro | Ser | Leu | Ser | Tyr | Met | Asp | Ile |
|     |     |     |     | 245 |     |     |     | 250 |     |     |     | 255 |
| Met | Arg | Asp | Val | Lys | Asn | Glu | Phe | Thr | Leu | Pro | Leu | Val | Ala | Tyr | Val |
|     |     |     | 260 |     |     |     | 265 |     |     |     | 270 |
| Ser | Gly | Glu | Tyr | Ser | Met | Val | Lys | Ala | Ala | Ala | Gln | Asn | Gly | Trp | Ile |
|     |     | 275 |     |     |     | 280 |     |     |     | 285 |     |
| Lys | Glu | Lys | Glu | Ile | Val | Leu | Glu | Ile | Leu | Thr | Ser | Met | Lys | Arg | Ala |
|     | 290 |     |     |     | 295 |     |     |     | 300 |     |     |
| Gly | Ala | Asp | Leu | Ile | Ile | Thr | Tyr | His | Ala | Lys | Asp | Ala | Ala | Lys | Trp |
| 305 |     |     |     | 310 |     |     |     | 315 |     |     |     | 320 |
| Leu | Ala | Glu |

( 2 ) INFORMATION FOR SEQ ID NO:23:

( i ) SEQUENCE CHARACTERISTICS:
        ( A ) LENGTH: 424 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:23:

| Met | Met | Ala | Ser | Thr | Phe | Asn | Ile | Pro | Cys | Asn | Ala | Gly | Thr | Ile | Lys |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |
| Asn | Phe | Asn | Asn | Ser | Gln | Arg | Asn | Leu | Gly | Phe | Ser | Ser | Asn | Leu | Gly |
|     |     |     | 20 |     |     |     | 25 |     |     |     | 30 |     |
| Ile | Asn | Phe | Ala | Lys | Thr | Arg | Phe | Ser | Asn | Cys | Gly | Asp | Ser | Gly | Arg |
|     |     | 35 |     |     |     | 40 |     |     |     | 45 |     |     |
| Ile | Pro | Ser | Gln | Leu | Val | Val | Arg | Ala | Ser | Glu | Arg | Arg | Asp | Asn | Leu |
|     | 50 |     |     |     | 55 |     |     |     | 60 |     |     |     |
| Thr | Gln | Gln | Lys | Thr | Gly | Leu | Ser | Ile | Glu | Glu | Cys | Glu | Ala | Ala | Val |
| 65 |     |     |     | 70 |     |     |     | 75 |     |     |     | 80 |
| Val | Ala | Gly | Asn | Ala | Pro | Ser | Ala | Pro | Pro | Val | Pro | Pro | Thr | Pro | Lys |
|     |     |     | 85 |     |     |     | 90 |     |     |     | 95 |
| Ala | Pro | Ser | Gly | Thr | Pro | Ser | Val | Ser | Pro | Leu | Ser | Leu | Gly | Arg | Arg |
|     |     |     | 100 |     |     |     | 105 |     |     |     | 110 |
| Pro | Arg | Arg | Asn | Arg | Thr | Ser | Pro | Val | Phe | Arg | Ala | Ala | Phe | Gln | Glu |
|     |     |     | 115 |     |     |     | 120 |     |     |     | 125 |

-continued

| | | | | | | | | | | | | | | |
|---|---|---|---|---|---|---|---|---|---|---|---|---|---|---|
| Thr | Thr 130 | Leu | Ser | Pro | Ala | Asn 135 | Val | Val | Tyr | Pro | Leu 140 | Phe | Ile | His | Glu |
| Gly 145 | Glu | Glu | Asp | Thr | Pro 150 | Ile | Gly | Ala | Met | Pro 155 | Gly | Cys | Tyr | Arg | Leu 160 |
| Gly | Trp | Arg | His | Gly 165 | Leu | Val | Glu | Glu | Val 170 | Ala | Lys | Ala | Arg | Asp 175 | Val |
| Val | Val | Asn | Ser 180 | Ile | Val | Val | Phe | Pro 185 | Lys | Pro | Asp | Ala | Leu 190 | Lys | Ser |
| Pro | Thr | Gly 195 | Asp | Glu | Ala | Tyr | Asn 200 | Glu | Asn | Gly | Leu | Val 205 | Pro | Arg | Thr |
| Ile | Arg 210 | Met | Leu | Lys | Asp | Lys 215 | Phe | Pro | Asp | Leu | Ile 220 | Ile | Tyr | Thr | Asp |
| Val 225 | Ala | Leu | Asp | Pro | Tyr 230 | Tyr | Tyr | Asp | Gly | His 235 | Asp | Gly | Ile | Val | Thr 240 |
| Gln | His | Gly | Val | Ile 245 | Met | Asn | Asp | Glu | Thr 250 | Val | His | Gln | Leu | Cys 255 | Lys |
| Gln | Ala | Val | Ala 260 | Gln | Ala | Arg | Ala | Gly 265 | Ala | Asp | Val | Val | Ser 270 | Pro | Ser |
| Asp | Met | Met 275 | Asp | Gly | Arg | Val | Gly 280 | Ala | Ile | Arg | Ala | Ala 285 | Leu | Asp | Ala |
| Glu | Gly 290 | Tyr | Ser | Asn | Val | Ser 295 | Ile | Met | Ser | Tyr | Thr 300 | Ala | Lys | Tyr | Ala |
| Ser 305 | Ser | Phe | Tyr | Pro | Arg 310 | Phe | Gly | Asp | Lys | Lys 315 | Thr | Tyr | Gln | Met | Asn 320 |
| Pro | Ala | Asn | Tyr | Arg 325 | Glu | Ala | Leu | Ile | Glu 330 | Thr | Gln | Glu | Asp | Glu 335 | Ser |
| Glu | Gly | Ala | Asp 340 | Ile | Leu | Leu | Val | Lys 345 | Pro | Gly | Leu | Pro | Tyr 350 | Leu | Asp |
| Ile | Ile | Arg 355 | Leu | Leu | Arg | Asp | Asn 360 | Ser | Asp | Leu | Pro | Ile 365 | Ala | Ala | Tyr |
| Gln | Val 370 | Ser | Gly | Glu | Tyr | Ser 375 | Met | Ile | Lys | Ala | Gly 380 | Gly | Val | Leu | Lys |
| Met 385 | Ile | Asp | Glu | Glu | Lys 390 | Val | Met | Leu | Glu | Ser 395 | Leu | Leu | Cys | Leu | Arg 400 |
| Arg | Ala | Gly | Ala | Asp 405 | Ile | Ile | Leu | Thr | Tyr 410 | Phe | Ala | Leu | Gln | Ala 415 | Ala |
| Arg | Cys | Leu | Cys 420 | Gly | Glu | Lys | Arg | | | | | | | | |